US006444644B1

(12) United States Patent
Bruckdorfer et al.

(10) Patent No.: US 6,444,644 B1
(45) Date of Patent: Sep. 3, 2002

(54) ANTICOAGULANT PEPTIDE FRAGMENTS DERIVED FROM APOLIPOPROTEIN B-100

(75) Inventors: Karl Richard Bruckdorfer; Camille Ettelaie, both of London (GB)

(73) Assignee: University College London, London (GB)

( * ) Notice: Subject to any disclaimer, the term of this patent is extended or adjusted under 35 U.S.C. 154(b) by 0 days.

(21) Appl. No.: 09/180,422

(22) PCT Filed: May 9, 1997

(86) PCT No.: PCT/GB97/01255

§ 371 (c)(1),
(2), (4) Date: Dec. 7, 1998

(87) PCT Pub. No.: WO97/43311

PCT Pub. Date: Nov. 20, 1997

(30) Foreign Application Priority Data

May 9, 1996 (GB) ............................................. 97/01255

(51) Int. Cl.$^7$ .......................... A61K 38/00; C07K 5/00; C07K 7/00

(52) U.S. Cl. ............................. 514/12; 514/2; 514/13; 514/14; 514/15; 514/16; 530/300; 530/324; 530/325; 530/326; 530/327; 530/328; 530/329; 530/350; 424/185.1

(58) Field of Search ........................ 514/2, 12, 15, 514/14, 13, 16; 530/300, 324, 350, 325, 326, 327, 328, 329; 424/185.1

(56) References Cited

FOREIGN PATENT DOCUMENTS

| WO | WO94/02446 | 2/1994 |
|---|---|---|
| WO | WO94/02447 | 2/1994 |
| WO | WO94/21625 | 9/1994 |
| WO | WO95/13289 | 5/1995 |

OTHER PUBLICATIONS

From British Society for Haemostasis and Thrombosis 10/96. Autumn meeting as follow: vol. 7, pp. 7–8.
Ettelaie et al *Blood Coagulation and Fibrinolysis* vol. 7, 1996, pp. 729–730 The inhibitory action of apolipoprotein B–100 towards thromboplastin, arises from the receptor binding domain of this protein.
Gleeson et al *Blood Coagulation and Fibrinolysis* vol. 7, 1996, pp. 732–733 Abstract P4 Inhibition of thromboplastin activity by the C–terminal of tissue factor pathway inhibitor (TFPI).
Wilbourn et al *Blood Coagulation and Fibrinolysis* vol. 7, 1996, p. 733 Abstract P5 The influence of LDL oxidation on the interaction of TFPI and thromboplasin.
Ettelaie, C., Howell, R.M., *Thombosis Research*, 1992, 68, 175–184.
Ettelaie, C. et al, *Arteriosclerosis, Thrombosis and Vascular Biology*, 16, 639–647, May 1996.
Ettelaie, C. et al, *Biochemica et Biophysica ACTA*, 1995, 1257, 25–30.
Ettelaie, C. et al, *Biochemica et Biophysica ACTA*, 1997, 1345, 237–247.
Yang et al, *Nature*, 323 738 (D3), Oct. 23, 1986.
Knott et al, *Nature*, 323 734 (D4), Oct. 23, 1986.
Chen et al, *Biochemistry*, 1989, 28 2477–84 (D5).
Nemerson, Y., Pepke, D., *Thromb. Res.*, 1985, 51, 165–713.
Nemerson, Y., *Blood*, 71, 1–8, Jan. 1988.
Howell, R.M., Ettelaie, C., *Biochem. Soc. Trans.*, 1989, 17, 576–577.
Howell, R.M., Ettelaie, C., *Biochem. Soc. Trans.*, 1990, 18, 680–681.
Goldstein, J.L., Brown, M.S., *Annu. Rev. Cell. Biol.*, 1985, 1, 1–39.
Chothia, C., Levitt, M., Richardson, D., *J. Mol. Biol.*, 1981, 145, 215–250.
Banner, D. W., D'Arcy, A., Chene, C., Winkler, F.K., Guha, A., Konigsberg, W. H., Nemerson, Y., Kirchhofer, D., *Nature*, 380, 41–46, Mar. 7, 1996.
Harlos, K., Martin, D.M.A., O'Brien, D.P., Jones, E.Y., Stuart, D.I., Polikarpov, I., Miller, A., Tuddenham, E.G.D., *Nature*, 370, 662–666, Aug. 25, 1994.
Ruf, W., Schullek, J.R., Stone, M.J., Edington, T.S., *Biochemistry*, 33, 1565–1572, 1994.
Girard, T.S., Warren, L.A., Novotny, W.F., Likert, K.M., Brown, S.G., Miletich, J.P., Broze, G. J., *Nature*, 338, 518–520, Apr. 6, 1989.
Chou, P. Y., Fasman, G.D., *Annu. Rev. Biochem.*, 1978, 47, 251–276.
Garnier, J., Osguthorpe, D.J., Robson, B., *J. Mol. Biol.*, 1978, 120, 97–120.
Jones, D., Taylor, W.R., Thornton, J.M., *Nature*, 358, 86, Jul. 2, 1992.
Milne, R., Theolis, R., Mautice, R., Pease, R., Weech, P., Rassar, E., Fruchart, J–C., Scott, J., Marcel, Y., *J. Biol. Chem.*, 264, 19754–19760, Nov. 25, 1989.
Law, A., Scott, J., *J. Lipid Res.*, 1990, 31, 1109–1119.
Chan, L., *J. Biol. Chem.*, 267, 25621–25624, Dec. 25, 1992.
Bach, R., Gentry, R. Nemerson, Y., *Biochemistry*, 4007–4020, vol. 25, No. 14, 1986.
Ettelaie et al, *Blood Coag. and Fibrinolysis*, 1996, 7, 7–8.
Malhotra et al, *Biochem J*, 1996, 314, 297–303.
*Blood Coag. Fibrinolysis*, 1996, 7, 5–14 Messier et al.,.
Ettelaie et al *Blood Coagulation and Fibrinolysis* vol. 7, 1996 p. 392 Abstract P11 "Comparison of the Inhibitory effects of TFPI and apolipoprotein B–100 . . . ".
Wilbourn et al *Blood Coagulation and Fibrinolysis* vol. 7, 1996, p. 392–393 Abstract P12 "TFPI–independent modulation of thromboplastin activity by LDL–the effects of oxidation".
Chen et al., *Biochemistry* , vol. 28, 1989, pp. 2477–2484.*
Knott et al., *Nature* , vol. 323, Oct. 1986, pp. 734–738.*
Yang et al., *Nature* , vol. 323, Oct. 1986, pp. 738–742.*

* cited by examiner

*Primary Examiner*—Avis M. Davenport
(74) *Attorney, Agent, or Firm*—Nixon & Vanderhye P.C.

(57) ABSTRACT

The present invention provides a peptide compound of formula $Z^1$—K—A—Q—$X^1$—K—K—N—K—H—R—H—S—$X^2$—T—$Z^2$ (SEQ ID NO:1) where: $X^1$ represents S or Y, $X^2$ represents T or I, $Z^1$ represents the N terminus of the peptide, or from 1 to 47 amino acids, $Z^2$ represents the C terminus of the peptide, a terminal amide group, or from 1 to 77 amino acids; or a variant of this peptide which contains one or more internal deletions, insertions or substitutions and which substantially retains anti-coagulant properties of apoB-100.

48 Claims, 6 Drawing Sheets

KRAD-14

ANTICOAGULANT PEPTIDE FRAGMENTS DERIVED FROM APOLIPOPROTEIN B-100

The present invention relates to peptides with anticoagulant properties. These are useful in a number of clinical applications, for example counteracting hypercoagulable states and in surgical procedures.

BACKGROUND TO THE INVENTION

The extrinsic pathway of coagulation is of central importance to the formation of thrombin in major blood vessels. This is initiated by the exposure of tissue factor (thromboplastin) from endothelial cells and monocyte/macrophages in the arterial wall.

Antidotes to tissue factor (TF), such as tissue factor pathway inhibitor, are found in the circulation associated with plasma proteins. However we have also found that plasma lipoproteins, particularly low density lipoproteins, can also exert an inhibitory effect on tissue factor activity (Ettelaie et al, 1995, Biochim. Biophys. Acta. 1257; 25–30).

The inhibition of TF is caused by the apolipoprotein B-100 (apoB-100). Its action is slower, but more long lasting than that of TFPI.

The exposure of thromboplastin, upon injury to endothelium, initiates the extrinsic pathway of coagulation and leads to formation of a blood clot on the injured surface [1, 2]. Following clot formation the procoagulant effect of thromboplastin is restrained by a number of circulating inhibitors within the serum. The ability of low density lipoprotein (LDL) [3–5] to inhibit the procoagulant activity of thromboplatin had been demonstrated previously. We have demonstrated that this inhibition arises from direct interaction of the protein moieties of thromboplastin (apoprotein III) and LDL (apolipoprotein B-100) [5–7]. Furthermore, the binding of the proteins involves the positively charged residues within apolipoprotein B-100 and negatively charged amino acids on thromboplastin [7]. We have previously identified a region within thromboplastin which closely resembled the repeated domains within the LDL-receptor protein, that are responsible for binding to apolipoprotein B-100 [7].

Inhibition of thromboplastin by apo B-100 may be disrupted with poly-L-lysine and to a lesser extent by poly-L-arginine [7]. Furthermore, blocking of lysine residues, e.g. during oxidation also seems to disrupt the inhibition [4,5].

DISCLOSURE OF THE INVENTION

Figure 1:
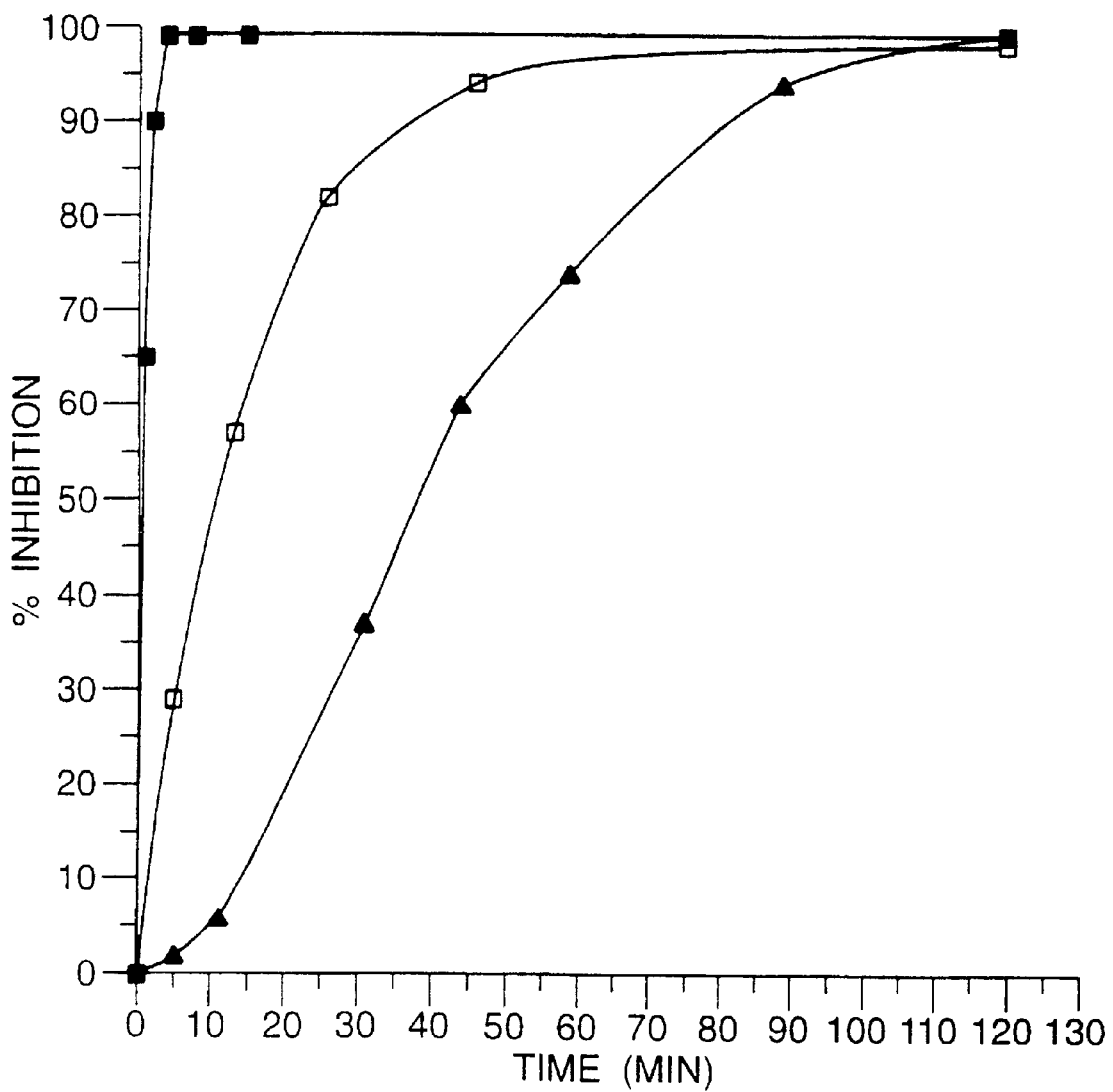
FIG. 1. Time-course assay of the inhibition of thromboplastin by KRAD-14, KRAD-98 and reconstituted apolipoprotein B-100.

By cloning and expression of a fusion protein containing the lysine-rich apolipoprotein B-100 derived (KRAD-14) peptide (14 amino acids long), we have explored the potential involvement of this domain in the interaction and inhibition of thromboplastin by apolipoprotein B-100.

Although apoB-100 is a very large protein with a molecular weight of about 515 kDa, we have surprisingly found that a small region within the protein is responsible for the inhibitory effect on TF. We have found that a peptide with a sequence derived from this region has much higher activity than apoB-100 itself. This peptide sequence is active when used in as a free peptide and also when present in a larger 98 amino acid sequence derived from apoB-100.

The KRAD-14 peptide has been examined against other coagulation factors. It seems to have an inhibitory effect against prothrombinase complex (factor Xa and factor V) in activating thrombin. The KRAD-14 peptide also has an ability to prevent the activation factor VII on the surface of thromboplastin. Furthermore, the KRAD-14 peptide seems to affect the activation of platelets by thrombin, probably due to prevention of the activation of thrombin. However, direct effect of KRAD-14 peptide on platelet activation cannot be ruled out.

In addition, recombinant thromboplastin (residues 58–66) was prepared and its effect on thromboplastin activity and inhibition by apolipoprotein B-100 was examined. It was demonstrated that this peptide is involved in the interaction of thromboplastin with apolipoprotein B-100.

Thus in a first aspect the present invention provides a peptide compound of formula:

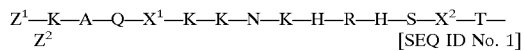

[SEQ ID No. 1]

where:
X$^1$ represents S or Y,
X$^2$ represents T or I,
Z$^1$ represents the N terminus of the peptide, or from 1 to 47 amino acids,
Z$^2$ represents the C terminus of the peptide, a terminal amide group, or from 1 to 77 amino acids;
or a variant of this peptide which contains one or more internal deletions, insertions or substitutions and which substantially retains anti-coagulant properties of apoB-100.

In the above formula the peptide sequence is represented by the standard 1-letter code.

The compound may be in the form of a salt, since it will comprise a number of acidic and basic side chains as well as, usually, a carboxy terminus.

The invention further provides a pharmaceutical composition comprising a compound of the formula (I) together with a pharmaceutically acceptable diluent or carrier.

The invention also provides a compound or composition of the invention for use in a method of treatment or therapy of the human or animal body. Such treatment includes the various treatments described below.

The invention also provides a method of treatment of hypercoagulable states which comprises administering to a patient in need of treatment an effective amount of the compound or composition according to the invention.

The invention also provides a method of reducing the risk of formation of undesired blood coagulation during a surgical procedure performed on a human or animal subject which comprises administering to the subject an effective amount of the compound or composition of the invention during surgery or post-operatively.

It is also known that some tumours secrete thromboplastin which is believed to assist in the process of metastasis. Prevention of metastasis is a major object of cancer therapy since a significant proportion of cancer deaths are attributable not to the primary tumour but to its metastatic spread. Thus in yet another aspect the present invention provides a method of reducing or preventing the process of metastasis in a human or animal subject suffering from a primary tumour which comprises administering to a patient in need of treatment an effective amount of the compound or composition according to the invention.

In this process, the compound or composition of the invention may be used in combination with other anti-metastatic compounds. Particular examples of such compounds includes matrix metalloproteinase inhibitors. Thus in a further aspect the invention provides a composition comprising a compound of the invention and a matrix metalloproteinase inhibitor.

The invention additionally comprises products containing a compound of the invention and a matrix metalloproteinase inhibitor as a combined preparation for simultaneous, separate or sequential use in cancer therapy.

DETAILED DESCRIPTION OF THE INVENTION

A. Compounds of Formula (I)

A.(i) When the N terminus of the compound of formula (I) shown as $Z^1$ is not simply the N terminal of the peptide it may comprise any suitable stretch of amino acids which allow the compound to retain anti-coagulant activity at least substantially similar to that found in apoB-100. The suitable stretch may comprise from 1 to 47, eg from 1 to 30, 1 to 20, or from 1 to 5 amino acids. The stretch of amino acids may be derived from apoB-100, for example they may represent the amino acids immediately to the N-terminal region of the 14 amino acids set out in Seq. ID No. 1. These N-terminal amino acids are set out as amino acids 1 to 47 in Seq. ID No. 12.

The region $Z^1$ may alternatively or in addition comprise a leader sequence. Such a sequence may be present when for example the compound of the invention is produced by recombinant means. In such a case the leader sequence will be selected to be compatible with the host cell in which the compound is produced. The leader sequence may for example direct expression of the compound through the cell wall.

The leader sequence may also contain a sequence susceptible of cleavage to release a peptide compound of the invention. Suitable leader sequences include the sequence DDDDK which is an enterokinase cleavage site. This may be placed in front of the sequence of the peptide of the invention when the peptide is produced by recombinant means.

A further possible option is that the group $Z^1$ represents methionine.

A.(ii) When the C terminus of the compound of formula (I) shown as "$Z^2$" is not simply the C terminal of the peptide (i.e. a carboxy group) it may comprise any suitable stretch of amino acids which allow the compound to retain anti-coagulant activity at least substantially similar to that found in apoB-100. The suitable stretch may comprise from 1 to 77, eg from 1 to 30, 1 to 20, 1 to 10 or from 1 to 5 amino acids. The stretch of amino acids may be derived from apoB-100, for example they may represent the amino acids immediately to the C-terminal region of the 14 amino acids set out in Seq. ID No. 1. These N-terminal amino acids are set out as amino acids 62 to 138 in Seq. ID No. 2.

The region $Z^2$ may alternatively or in addition comprise a signal sequence. Such a sequence may be present when for example the compound of the invention is produced by recombinant means. In such a case the signal sequence will be selected to be compatible with the host cell in which the compound is produced. The signal sequence may for example direct expression of the compound through the cell wall or to a particular cellular compartment.

The leader sequence may also contain a sequence susceptible of cleavage to release a compound of formula (I). Suitable cleavage sites include the sequences mentioned above in section A(i).

Preferably, $Z^2$ represents a carboxy group.

A.(iii) Peptides of the invention include fragments of Seq. ID No. 1, particularly fragments which retain the motif KKNK, preferably $X^1$KKNKH where $X^1$ is as defined above.

Thus for example fragments of the peptide of Seq. ID No. 1 include:

| | |
|---|---|
| Q-$X^1$-K-K-N-K-H-R | [SEQ ID No. 2] |
| A-Q-$X^1$-K-K-N-K-H | [SEQ ID No. 3] |
| A-Q-$X^1$-K-K-N-K-H-R | [SEQ ID No. 4] |
| Q-$X^1$-K-K-N-K-H-R-H | [SEQ ID No. 5] |
| A-Q-$X^1$-K-K-N-K-H-R-H | [SEQ ID No. 6] |
| Q-$X^1$-K-K-N-K-H-R-H-S | [SEQ ID No. 7] |
| A-Q-$X^1$-K-K-N-K-H-R-H-S | [SEQ ID No. 8] |
| K-A-Q-$X^1$-K-K-N-K-H-R-H-S | [SEQ ID No. 9] |
| A-Q-$X^1$-K-K-N-K-H-R-H-S-$X^2$ | [SEQ ID No. 10] |
| K-A-Q-$X^1$-K-K-N-K-H-R-H-S-$X^2$ | [SEQ ID No. 11] |

Variants of fragments include substitutions of one or more (e.g up to 4) amino acids. Preferred substitutions are conservative substitutions. Substitutions of this type may be made for a variety of reasons. For example, as demonstrated below, the residues $X^1$ and $X^2$ in apoB-100 are normally Y and I respectively, but these have been changed to S and T respectively to increase the solubility of the peptide. Similar types of changes may be made to the other amino acids of the peptide where this does not alter the activity to any significant degree.

Conservative substitutions may be made according to the following table, where amino acids on the same block in the second column and preferably in the same line in the third column may be substituted for each other:

| ALIPHATIC | Non-polar | G A P |
|---|---|---|
| | | I L V |
| | Polar-uncharged | C S T M |
| | | N Q |

| | Polar-charged | D E |
| --- | --- | --- |
| | | K R |
| AROMATIC | | H F W Y |
| OTHER | | N Q D E |

A.(iv) Insertions to the sequence of formula (I) may also be made. One or more amino acids (e.g. up to 4) may be inserted at any position in the sequence of the compound. Preferably, any insertions made will be selected to avoid major changes to tertiary structure. This can be calculated using commercially available algorithms and tested empirically using methods described herein.

A.(v) Where the peptide of the invention comprises N- and/or C-terminal extensions such extensions are desirably based upon the sequence of apoB-100 itself.

Such peptides are up to 138 amino acids in size, and comprise all of all part (as defined below) of the sequence:

```
  1          11         21         31         41         51         [SEQ ID NO. 12]
  NIPLTIPEMR LPYTIITTPP LKDESLWEKT GLKEFLKTTK QSFDLSVKAQ YKKNKHRHSI 61          71         81         91        101        111
  TNPLAVLCEF ISQSIKSFDR HFEKNRNNAL DFVTKSYNET KIKFDKYKAE KSHDELPRTF 121         131
  GIPGYTVPVV NVEVSPFT
``` where Y at position 51 may also be S and I at position 60 may also be T.

Where part of the sequence of Seq. ID No. 12 is referred to, it will be understood that such a portion of the sequence will comprise the motif KKNK, preferably $X^1$KKNKH where $X^1$ is as defined above, and more preferably any one of the sequences set out above as Seq ID Nos. 2–11.

A preferred portion of the peptide of Seq. ID No. 2 is the 98 amino acid sequence from position 21 (L) to 118 (R).

However, portions of any contiguous 15, e.g 20, 30, 40, 50, 60, 70, 80, 90, 100, 110 or 120 amino acids of the sequence may be used provided such portions retain the KKNK motif as described above.

It will also be understood that modifications to the sequence of Seq ID No. 12 may be made provided such modifications do not substantially alter the activity of such a sequence or portions thereof compared to the unaltered sequence or portion thereof respectively. Such modifications include one or more (e.g. up to about 15% of the number of total residues in the peptide) substitutions, particularly conservative substitutions as defined above, and/or one or more (e.g. up to about 15% of the number of total residues in the peptide) deletions.

Computer modelling suggests that, within apolipoprotein B-100, the domain including KRAD-98 and KRAD-14 (amino acids 3121–3217) is structurally closely associated with another positively charged sequence, in the region of amino acids 3300–3400. More specifically, the positively charged sequence is believed to be RLTRKRGLKLAT (SEQ ID No. 13), which is the sequence of amino acids 3359–3367 of apolipoprotein B-100 (see below) Therefore, this sequence may be able to enhance the activity of the peptides of SEQ ID No.1.

Therefore, in preferred embodiments of the invention, a first peptide of SEQ ID No. 1, or a variant thereof as defined herein, is associated with a second peptide which comprises amino acids 3300–3400 of apolipoprotein B-100, or a part or variant thereof as defined below. The two peptides may be physically attached in any way. For example, the second peptide may be provided as an N-terminal or C-terminal extension of the peptide of SEQ ID No.1, joined by a peptide bond, or it may be attached in some other way, for example by one or more covalent linkages, such as cysteine-cysteine disulphide linkages. The attachment can be made by means known in the art.

Alternatively, the second peptide may be physically unattached to the peptide of SEQ ID No. 1 but administered together with it. Thus, the invention provides pharmaceutical compositions comprising peptides of SEQ ID No. 1 and a second peptide which comprises amino acids 3300–3400 of apolipoprotein B-100, or a variant thereof as defined below, together with a pharmaceutically acceptable carrier.

The second peptide may include the entire sequence of amino acids 3300–3400 of apolipoprotein B-100. Most preferably, the second peptide consists of amino acids 3300–3400 of apolipoprotein B-100. However, the second peptide may have more or less than the sequence of amino acids 3300–3400 of apolipoprotein B-100, or have a sequence differing from that of amino acids 3300–3400 of apolipoprotein B-100 as long as the second peptide enhances the activity of the peptide of SEQ ID No. 1. For example, the second peptide may contain one or more internal deletions, insertions or substitutions, as defined herein for the peptides of SEQ ID No. 1.

Similarly, the second peptide may be extended, in the sense that it may contain extensions at one or both ends. These extensions may be the sequences that are adjacent to the second peptide in apolipoprotein B-100 or any other sequence. The extension or extensions may be of any length, for example 1 to 10, 10 to 20, or 20 to 50 amino acids.

Similarly, the second peptide may be truncated with respect to amino acids 3300–3400, as long as it retains the ability to enhance the activity of the first peptide. For example, the truncated second peptide may be up to 20, up to 50, up to 80, up to 90, up to 95 or up to 99 amino acids in length.

More particularly, the second peptide may comprise the positively charged sequence, SEQ ID No. 13. For example, the second peptide may have exactly the sequence of SEQ ID No. 13 or it may be contain one or more deletions, insertions or substitutions as defined herein for the peptide of SEQ ID No. 1. Similarly, it may be extended or truncated as defined above as long as it retains the ability to enhance the activity of the first peptide.

In the sequence of apolipoprotein B-100 (see below), both KRAD-14 and the sequence of SEQ ID No. 13 are underlined. Also, two cysteine residues (3167 and 3397) are underlined. Where the first and second peptides are joined by cysteine-cysteine covalent linkages, these two cysteines may conveniently be used. Alternatively, if the particular peptides being used do not include both of those cysteine residues, other means of attachment may be used. In particular, additional cysteine residues may be incorporated into the first and/or second peptides to facilitate their attachment. This can be done by routine techniques of peptide synthesis already known in the art.

A.(vi) Peptides of the invention and the variants described above may be made by any suitable means available to those of skill in the art. The compounds may be made synthetically or by recombinant means.

Synthetic production of peptides is well known in the art and is available commercially from a variety of companies. Recombinant production may be achieved via the use of a nucleic acid (preferably DNA) encoding the sequence of the compound of formula (I) operably linked to a promoter for the expression of the said DNA and optionally a regulator of the promoter. This construct will be placed in a vector which may be, for example, a plasmid, virus or phage vector provided with an origin of replication. The vector may contain one or more selectable marker genes, for example an ampicillin resistance gene in the case of a bacterial plasmid or a neomycin resistance gene for a mammalian vector. The vector may be used to transfect or transform a host cell. Suitable cloning and expression vectors are available commercially and can be used for this purpose.

Vectors comprising nucleic acid encoding the peptides of the invention themselves form a further aspect of the invention.

A further embodiment of the invention provides host cells transformed or transfected with the vectors of the invention for the replication and expression of vectors according to the invention. The cells will be chosen to be compatible with the vector and may for example be bacterial, yeast, insect or mammalian.

Conditions for the expression of foreign proteins in expression vectors are well known in the art and may be utilized to express a compound of the invention in the host cell and recover said compound in purified form.

A.(vii) The amino acid sequence of the peptides of the invention may also be modified to include non-naturally-occurring amino acids or to increase the stability of the compound in vivo. When the compounds are produced by synthetic means, such amino acids may be introduced during production. The compound may also be modified following either synthetic or recombinant production.

Peptides of the invention which are of a size suitable for synthetic production may also be made using D-amino acids. In such cases, the amino acids will be linked in a reverse sequence in the C to N orientation. This is conventional in the art for producing such peptides.

The carboxy terminus and any other carboxy side chains may be blocked in the form of an ester group, e.g. a $C_{1-6}$ alkyl ester.

Salts of compounds of the invention which may be conveniently used in therapy include physiologically acceptable base salts, eg derived from an appropriate base, such as alkali metal (e.g. sodium), alkaline earth metal (e.g. magnesium) salts, ammonium and $NR_4$ (wherein R is $C_{1-4}$ alkyl) salts. Salts also include physiologically acceptable acid addition salts, including the hydrochloride and acetate salts.

A. (viii) As mentioned above, variants of the compounds of the formula (I) which are included within the scope of the invention are those which substantially retain the anti-coagulant properties of apoB-100. This may be determined by making such variants and assaying them by methods described in the examples for their ability to inhibit the activity of thrombin. Variants which show activity which is at least 0.1 fold, preferably 0.5 fold, the activity of apoB-100 are considered as retaining the necessary anti-coagulant activity. This may be determined by any suitable assay, for example the thromboplastin activity assay illustrated in the accompanying examples.

B. Compositions of the Invention

B.(i) Pharmaceutically acceptable carriers or diluents include those used in formulations suitable for oral or parenteral (e.g. intramuscular or intravenous) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

For example, formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents, and liposomes or other microparticulate systems which are designed to target the polypeptide to blood components or one or more organs.

Suitable liposomes include, for example, those comprising the positively charged lipid (N[1-(2,3-dioleyloxy) propyl]-N,N,N-triethylammonium (DOTMA), those comprising dioleoylphosphatidylethanolamine (DOPE), and those comprising 3β[N-(n',N'-dimethylaminoethane)-carbamoyl]cholesterol (DC-Chol).

Optionally, the peptides of the invention may be attached to drug delivery substrates in order to facilitate their delivery to the correct location in the patient. Suitable substrates include polymeric beads known in the art. Such beads may, preferably, be engineered to target the peptides of the invention to a given location in the body.

C. Treatment of Hypercogulable States

There are a number or medical conditions where patients are at risk from blood clotting which may benefit from administration to the patient of a peptide of the invention. These include patients suffering from chronic cardiovascular conditions as well as acute thrombotic episodes, e.g heart attacks or strokes. Administration of a peptide of the invention to such patients will help reduce the risk of such conditions or their recurrence following a thrombotic episode.

D. Treatment During Surgical Procedures

There are many types of surgical procedure where the risk of blood coagulation during surgery or post operatively may be reduced by use of the compound of the invention. Such procedures include coronary reperfusion, transplantation of organs (e.g. liver, kidney, heart or lung transplantations), and major surgery such as open heart surgery.

E. Prevention or Reduction of Metastasis

Metastases are associated with almost every type of cancers. These include colon, ovarian, breast, prostate, lung (including small cell lung), stomach and liver cancers. Preventing or reducing metastatic spread represents a major goal of current cancer research. Reducing the spread includes both reducing the number of metastases which are established in a patient as well as reducing the rate at which metastases grow by invasion of normal tissue.

All the above-mentioned tumour types are candidates for treatment with compounds of the invention for the prevention or reduction of metastatic spread. Preferred tumour types are those where thromboplastin is being expressed by the primary tumour.

The peptide compounds of the invention may be administered in conjunction with other anti-tumour agents, particularly agents which also prevent or inhibit metastatic spread. Suitable other anti-metastatic compounds include matrix metalloproteinase (MMP) inhibitors.

Such inhibitors are well known in the art and include hydroxamic acid based MMP inhibitors of the general structure:

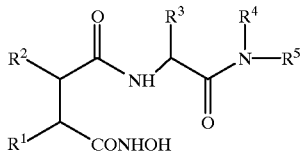

wherein the five substituents $R^1$ to $R^5$ may vary. Examples of such compounds may be found in several patent publications including US-A-4599361, EP-A-231081, EP-A-236872, EP-A-274453, WO90/05716, WO90/05719, WO91/02716, WO92/09563, EP-A-497192, WO92/13831, EP-A-489577, EP-A-489579, WO92/22523, US-A-6256657, WO93/09090, WO93/09097, WO93/20047, WO93/21942, WO93/24449, WO93/24475, EP-A-574758, WO94/02446, WO94/02447 and WO94/21625, the disclosures of which are incorporated herein by reference.

Suitable values of the group $R^1$ include hydrogen, $C_{1-6}$ alkyl, $C_{2-6}$ alkenyl, phenyl, phenyl $C_{1-6}$ alkyl, $C_{1-6}$ alkylthiomethyl, phenylthiomethyl, phenyl $C_{1-6}$ alkylthiomethyl or hetrocyclylthiomethyl where hetrocyclyl is as defined below.

Suitable values of $R^2$ include a $C_2-C_6$ alkyl group which may contain an ether or thioether linkage; Suitable values of $R^3$ include (a) the side chain of a naturally occurring alpha-amino acid in which any carboxylic acid groups may be esterified or amidated, any hydroxyl or thiol groups may be acylated or alkylated (etherified) and any amino groups may be acylated, or (b) a group $R^6$ $(A)_{n-}$ wherein n is 0 or 1, A represents a divalent $C_1-C_6$ alkyl or $C_2-C_6$ alkenyl group optionally interrupted by one or more —O—, or —S— atoms or —N($R^7$)— groups where $R^7$ is hydrogen or $C_1-C_6$ alkyl, and $R^6$ is a phenyl or heterocyclyl group either of which may be substituted, or (except where n is O) a hydrogen atom.

Suitable values of $R^4$ include hydrogen or methyl.

Suitable values of $R^5$ include hydrogen, $C_1-C_6$ alkyl or phenyl ($C_1-C_6$ alkyl).

The term "$C_1-C_6$ alkyl" refers to a straight or branched chain alkyl moiety including for example, methyl, ethyl, propyl, isopropyl and isobutyl.

Groups which may contain an ether or thioether linkage include $CH_3(CH_2)_2OCH_2$—, and $CH_3(CH_2)_2S$—.

The term "$C_2-C_6$ alkenyl" refers to a straight or branched chain alkenyl moiety having from 2 to 6 carbon atoms and having in addition one double bond of either E or Z stereochemistry where applicable.

The term "side chain of a naturally occurring alpha-amino acid" includes the side chains of the twenty naturally occurring amino acids encoded by the genetic code as well as naturally occurring substances such as S-hydroxylysine and 4-hydroxyproline. The amino acid side chains may be protected; for example the carboxyl groups of aspartic acid and glutamic acid may be esterified (for example as a $C_1-C_6$ alkyl ester), the amino groups of lysine, 5-hydroxylysine, 4-hydroxyproline may be converted to amides (for example as a $COC_1-C_6$ alkyl amide) or carbamates (for example as a $C(=O)OC_1-C_6$ alkyl or $C(=O)OCH_2Ph$ carbamate).

The term "heterocyclyl" refers to a 5–7 membered heterocyclic ring containing one or more (e.g. 2) heteroatoms selected from S, N and O, and optionally fused to benzene ring, including for example, pyrrolyl, furyl, thienyl, imidazolyl, pyridinyl, pyrrolidinyl, pyrimidinyl, morpholinyl, piperizinyl and indolyl.

MMPs may be used in the form of salts including physiologically acceptable acid addition salts for example hydrochlorides, hydrobromides, sulphates, methane sulphonates, p-toluenesulphonates, phosphates, acetates, citrates, succinates, lactates, tartrates, fumarates and maleates, Salts may also be formed with bases, for example sodium, potassium, magnesium, and calcium salts.

There are several chiral centres in the MMP compounds because of the presence of asymmetric carbon atoms. The presence of several asymmetric carbon atoms gives rise to a number of diastereomers with R or S stereochemistry at each chiral centre. Unless specified otherwise all other formulae in this specification are to be understood to include all such stereoisomers and mixtures (for example racemic mixtures) thereof. The preferred stereochemistry is in general as follows:

C atom carrying the $R^1$ group and hydroxamic acid moiety —S,

C atom carrying the $R^2$ group —R,

C atom carrying the $R^3$ group —S, but mixtures in which the above configurations predominate may also be used.

A particular example of such a compound is [4-N-hydroxyamino)-2R-isobutyl-3S-(thienyl-thiomethyl) succinyl]-L-phenylalanine-N-methylamide (known as Batimastat or "BB-94").

MMPs may be administered by any suitable route and in any formulation, for example those comprising a liquid or solid diluent or carrier. Oral administration, for example in tablet form, is one suitable route. Doses will be at the discretion of the physician depending upon the properties of the particular MMP and the nature of the condition being treated. Suitable doses include those in the range of from 0.1 to 300, e.g from 1 to 100 mg/kg body weight per day.

F. Prevention of other Thromboplastin-Related Phenomena

The inhibitory effect of the KRAD-14 peptide against thromboplastin may result in the prevention of other processes related to thromboplastin e.g. angiogenesis, cellular differentiation and apoptosis. Thus, the peptides of the invention may also be useful in the inhibition of these processes, and other (100 thromboplastin-related processes.

G. Routes of Administration and Doses of Peptides of the Invention

G.(i) Suitable routes of administration of peptides of the invention include oral or parenteral, and will depend in part upon the intended use and the discretion of the physician. Small peptides may be administered orally although parenteral administration may generally be more convenient in some circumstances. For example, during surgical procedures the compounds may be administered via drips used to deliver blood and/or saline during surgery.

G. (ii) Although the amount of peptides of the invention administered to a patient is ultimately at the discretion of the physician, taking account of the condition of the patient and the condition to be treated, typical amounts of compounds of the invention-required to achieve an anti-coagulant effect will be effective to deliver a concentration of peptide in the region of from 0.1 $\mu$M to 10 mM, e.g from 1 $\mu$M to 1 mM in the body of a patient. This may be achieved using doses of about from 0.1 mg to 10 g, eg. 1 mg to 1 g per Kg body weight per day.

The following examples illustrate the invention.

Materials and Methods

Oligonucleotide synthesis was carried out on a Biosearch Cyclone oligonucleotide synthesiser (PerSeptive Biosystems Inc., Biosearch Products, U.K.) using reagents purchased from Cambio Ltd (Cambridge, U.K.). Pinpoint Xa protein expression kit, Wizard PCR preps kit, Wizard miniprep kit, Chromatophor protein visualisation system, streptavidin-alkaline phosphatase conjugate, Hind III and Not I restriction enzymes, T4 DNA ligase, Taq polymerase, *E.coli* (JM103) cells, nitro blue tetrazolium and bromochloroindoyl phosphate were obtained from Promega Corporation, Southampton, U.K.). Deoxynucleotides and ampicillin were from Gibco Life Sciences (Paisley, Scotland) and enterokinase, chymotrypsin, N-benzoyl-phe-val-arg-p-nitroanilide (for the two stage amidolytic assay), isopropyl-$\beta$-thiogalactopyranoside, biotin and Terrific broth were obtained from Sigma Chemical Company Ltd. (Poole, U.K.). The apolipoprotein B-100 control peptide (fragment 3358–3372) containing the sequence TRLTRKRGLKLA-TAL was also purchased from Sigma Chemical Company Ltd. (Poole, U.K.). Protean II electrophoresis and blotting apparatus was from Bio Rad (Hemel Hempstead, U.K.). Recombinant thromboplastin was from Gamidor Ltd. (Oxfordshire, U.K.). Control plasma (NormTrol), for the one-stage prothrombin time assay, was purchased from Helena Laboratories (Tyne and Wear, U.K.). A synthetic peptide with a sequence identical to that of chymotrypsin-released KRAD-14 was purchased to order, from the in-house peptide synthesis facility.

Cloning and Expression of Peptides

In order to minimise the possibility of peptide aggregation due to presence of hydrophobic amino acids the peptide sequence (KAQSKKNKHRHSTT (Seq. ID No. 1)) was prepared instead of the parent (KAQYKKNKHRHSIT (Seq. ID No. 1)). The secondary structure of the peptide was not compromised by these substitutions as determined by prediction methods [17, 18]. Both the coding and non-coding strands were synthesised on the oligonucleotide synthesiser. The coding region was preceded by a codon for a single tyrosine to define a cleavage site for chymotrypsin. The oligonucleotides were prepared to encode a Hind III site at the 5' end of the coding site and a Not I site at the 3' end, as shown below;

5' AGCTTTATAA AGCTCAGTCC AAAAAAAACA AACACCGTCA CTCCACCACC TAAGC 3'
AATATT TCGAGTCAGG TTTTTTTTGT TTGTG-GCAGT GAGGTGGTGG ATTCGCCGG

Plasmid Pinpoint Xa(3) was digested with Hind III and Not I overnight at 4° C., and an aliquot was examined on agarose gel in order to confirm complete digestion. The excised fragment was removed using the Wizard PCR preps kit. Following deprotection and isolation, the KRAD-14 oligonucleotide insert was ligated into Pinpoint plasmid using T4 DNA ligase at 4° C. overnight.

KRAD-98 peptide (98 amino acids) corresponded to residues 3121–3217 of apolipoprotein B-100 sequence and residues 21 to 118 of Seq. ID No. 12. Overlapping strands of DNA (each 200 bp long) with non-identical termini, to enable unidirectional cloning, were engineered using the oligonucleotide synthesiser. An enterokinase cleavage site was included immediately preceding the apolipoprotein B-100-peptide sequence, this site is later used to release the biotinylated protein. Following deprotection and isolation, the two strands were heated together at 95° C. for 1 min and annealed by progressive cooling down to 50° C. The strands were completed by addition of Taq polymerase (3 units) and 0.2 mM nucleotide solution. The product was examined by agarose gel electrophoresis. The KRAD-98DNA was then digested with Hind III and Not I overnight at 4° C.

Similarly, the DNA sequence (shown below) coding for thromboplastin residues 58–66 (DLTDEIVKD) was prepared and cloned and the peptide expressed and isolated as described. 5' AGCTTTATGA CCTGACCGAC GAAATCGTGA AAGACTAAGC 3' AATACT GGACTG-GCTG CTTTAGCACT TTCTGATTCG CCGG Competent *E. coli* (JM109) cells were subsequently transfected with either, the plasmid containing the KRAD-14 insert, KRAD-98 insert, thromboplastin fragment (58–66) insert, plasmid without any insert or with Pinpoint control plasmid (containing the chloramphenicol acetyltransferase gene as a fusion peptide) and selected by growth in Terrific broth, containing ampicillin (100 $\mu$g/ml). The cells were then grown in the presence of 100 $\mu$g/ml isopropyl-$\beta$-thiogalactopyranoside (IPTG) and 5 $\mu$g/ml biotin. The cells were harvested by centrifugation and washed in isolation buffer (50 mM Tris-HCl, 2 mM EDTA pH 7.8). The cells were then lysed by sonication in isolation buffer. The biotinylated proteins were isolated using the Softlink matrix (supplied with the pinpoint protein expression kit) according to the manufacturer's instructions. The peptide samples were then dialysed and freeze-dried.

Western Blotting

SDS-polyacrylamide electrophoresis was carried out using a Protean II apparatus. A 12% (w/v) acrylamide gel was prepared using the Chromatophor protein visualisation system and according to the manufacturer's instructions. The gel was then blotted onto nitrocellulose, blocked for 60 min with Tris buffer, saline Tween (TBST) (10 mM Tris-HCl pH. 8.0, 150 mM NaCl, 0.05% w/v Tween 20) and incubated for 30 min with streptavidin-alkaline phosphatase conjugate in TBST. The membrane was then washed three times with TBST and once with distilled water. Finally, the membrane was probed with nitro blue tetrazolium/bronochloroindolyl phosphate (NBT/BCIP).

Release of the Biotinylated Tag Using Chymotrypsin or Enterokinase

In order to release the KRAD-14 peptide from the biotinylated fusion protein, aliquots (0.5 mg/ml) of the isolated fusion protein were incubated with bovine pancreatic chymotrypsin (0.1 mg/ml final concentration). To release KRAD-98, aliquots (0.5 mg/ml) of the isolated fusion protein were incubated with enterokinase (0.1 mg/ml final concentration). In addition an equal volume of distilled water was treated with the same amount of chymotrypsin or enterokinase to ensure that at the concentrations used, the enzymes did not have a significant effect on the thromboplastin activity. The biotinylated tag was then removed by chromatography using the Softlink column as before. The digested samples were then examined on a 15% (w/v) SDS-acrylamide gel to ensure proper release of the protein, as before and the bulk of the sample freeze dried.

Isolation and Reconstitution of Apolipoprotein B-100

Low density lipoproteins (LDL) were prepared by ultracentrifugation [19] and apolipoprotein B-100 was isolated by delipidation and gel filtration and reconstituted (1 mg/ml) in phosphatidylcholine (1 mg/ml) as described previously [5, 19–21].

Measurement of Thromboplastin Activity

The one stage prothrombin time assay was carried out by the addition of 100 µl of the sample to 100 µl of 25 mM CaCl$_2$ solution and incubation prior to addition of 100 µl of control plasma. The clotting time was measured on the coagulometer. The two-stage amidolytic assay was carried according to published procedures [9]. In all cases the thromboplastin activity was calculated from a standard curve prepared previously and the percentage inhibition was calculated as 100×(Initial activity/Residual activity)/Initial activity.

Measurement of the Effects of Apolipoprotein B-100-Derived Peptides on Thromboplastin Activity The apolipoprotein B-100 control peptide (fragment 3358–3372) containing the sequence TRLTRKRGLKLA-TAL was reconstituted in distilled water to 1 mM. The freeze-dried samples were reconstituted in distilled water to a concentration of 1 mM. Two 200 µl samples of thromboplastin (10 U/ml) were incubated with 500 nM KRAD-14 or apolipoprotein B-100 control peptide at 37° C. for 45 min. Another set of 200 µl samples of thromboplastin (10 U/ml) were incubated with either 500 nM KRAD-98 or the chloramphenicol acetyltransferase control protein. Finally, another 200 µl of thromboplastin was incubated with 500 nM reconstituted apolipoprotein B-100 [5] or equal amount of distilled water. Following the incubation the thromboplastin activity in all the samples was measured by means of the one-stage prothrombin time assay and the two-stage amidolytic assay and the percentage inhibition calculated against the control containing distilled water.

The above experiments were repeated using 1 ml samples containing recombinant thromboplastin (10 U/ml) mixed with either 500 nM KRAD-14, 500 nM KRAD-98 or 500 nM apolipoprotein B-100, reconstituted as described before [5]. The concentrations used are equivalent to that of apolipoprotein B-100 in normal plasma [8]. 100 µl of the each sample was removed immediately and assayed for thromboplastin activity, by means of the one-stage prothrombin time assay. The rest of the samples were incubated at 37° C. and further 100 µl samples were removed at intervals up to 120 min and measured as before. The percentage inhibition was calculated against a control sample of thromboplastin.

In order to monitor the inhibitory potential of the isolated peptides in the presence of plasma, aliquots (100 µl) of the recombinant thromboplastin (10 U/ml) were incubated for 5 min, with equal amounts of either KRAD-14 or for 40 min with equal volumes of either KRAD-98 in the presence and absence of plasma, at 37° C. The samples were then assayed by addition of 100 µl of 25 MM CaCl$_2$ solution and measurement on the coagulometer. The percentage inhibition in each case calculated against a similarly treated sample, containing thromboplastin only.

The synthetic KRAD-14 peptide was reconstituted in distilled water at 1 mM. Aliquots of recombinant thromboplastin were incubated, at 37° C. with a KRAD-14 at concentration range 10–5000 nM (final concentration) for 1 min prior to assaying using the one-stage prothrombin time assay. In addition, samples of thromboplastin (10 U/ml) were incubated with synthetic KRAD-14 at concentrations ranging from 1–100 µM (final concentration) prior to assaying using the one-stage prothrombin time assay.

In other experiments, recombinant thromboplastin (1 mg/ml) was delipidated with chloroform/methanol as described previously [5,19], to remove phosphatidylserine and other lipids and reconstituted with phosphatidylcholine (1 mg/ml) to differentiate between the effects of the prepared samples on the protein moiety of thromboplastin and any effects on the thromboplastin-associated phosphatidylserine. Aliquots of recombinant thromboplastin (1 mg/ml) were incubated with KRAD-14 peptide (500 nM), KRAD-98 (500 nM) peptide, reconstituted apolipoprotein B-100 (500 nM) or each of the control peptides (500 nM) for 30 min prior to assaying using the one-stage prothrombin time and the two-stage amidolytic assay. The percentage inhibition was calculated against the control sample.

Measurement of Influence of KRAD-14 on Thrombin Activity

Samples (1 ml) of either KRAD-14 peptide (500 nM) or each of the control peptides (500 nM) were incubated with thrombin (100 nM) at 37° C. and the thrombin activity measured at the beginning and at intervals up to 60 min as follows. The enzymatic activity of thrombin was measured by the addition of 100 µl aliquots to 0.45 ml of thrombin substrate (N-benzoyl-phe-val-arg-p-nitroanilide) (0.26 mM) which was then incubated at 37° C. for exactly 10 min, before the addition of 0.45 ml of 20% (w/v) acetic acid. The absorption was measured at 405 nm against a thrombin (100 nM) control assayed similarly. The procoagulant activity of thrombin was measured by the addition of 100 µl of the sample to control plasma (100 µl) and 25 mM CaCl$_2$ solution and measuring the clotting time. A thrombin 100 nM) control was included in the assay against which comparisons were made.

Measurement of Influence of KRAD-14 on Factor Xa Activity

Samples (1 ml) of either KRAD-14 peptide (500 nM) or the control peptide 500 nM) were incubated with pre-activated factor Xa (100 nM) at 37° C. and the factor Xa activity measured at the beginning and at intervals up to 60 min as follows. The enzymatic activity of factor Xa was measured by the addition of 100 µl aliquots to 0.45 ml of thrombin substrate (N-benzoyl-ile-glu-gly-arg-p-nitroanilide) (0.26 mM) which was then incubated at 37° C. for exactly 10 min, before the addition of 0.45 ml of 20% (w/v) acetic acid. The absorption was measured at 405 nm against a factor Xa (100 nM) control assayed similarly. The procoagulant activity of factor Xa was measured by the addition of 100 µl of the sample to factor Xa-deficient plasma (100 µl) and 25nM CACl$_2$ solution and measuring the clotting time. A factor Xa (100 nM) control was included in the assay against which comparisons were made.

Measurement of Influence of KRAD-14 on Factor V Activity

Samples (1 ml) of either KRAD-14 peptide (500 nM) or the control peptide (500 nM) were incubated with pre-activated factor V (100 nM) at 37° C. and the factor V activity measured at the beginning and at intervals up to 60 min as follows. The procoagulant activity of factor V was measured by the addition of 100 µl of the sample to factor V-deficient plasma (100 μl) pre-activated by incubation (2 min) with thromboplastin (200 nM) in the presence of CaCl₂ (25 mM), and measuring the clotting time. The activity was measured against a standard curve and the percentage inhibition calculated against the initial factor V activity. The curves are typical of data from three separate experiments.

Measurement of the Effect of KRAD-14 on the Activation and Activity of Factor VII In order to assess whether the action of KRAD-14 peptide was directed to the proteolytic activity of factor VIIa/thromboplastin or the activation of factor VII by interaction with thromboplastin, first thromboplastin (200 nM) and factor VII (200 nM) were incubated for 10 min in the presence of 25 mM CaCl₂, prior to addition of KRAD-14 peptide and a further 10 min incubation. The samples were then assayed by addition to factor VII deficient plasma and measuring the clotting time. Appropriate controls devoid of KRAD-14 peptide were included in each experiment.

Measurement of the Effects of Thromboplastin Peptide (58–66) on Thromboplastin Activity and Inhibition The control peptide (VQGEESDNK) was reconstituted to 1 mM in distilled water. The control peptide was similar but not identical to the thromboplastin (58–66), in size, charge and amino acid composition but with a different sequence. In order to assess the effect of the thromboplastin peptide (58–66) on the activity of thromboplastin, samples of recombinant thromboplastin (100 nM) were incubated for 5 min, with the isolated thromboplastin-peptide (1 μgM), control peptide (1 μM) or distilled water at 37° C. prior to assaying using the one-stage prothrombin time assay. The activity was calculated from a thromboplastin standard curve.

To demonstrate the ability of the peptide to influence the interaction of thromboplastin with apo B-100 samples of recombinant thromboplastin (100 nM) were incubated with reconstituted apoB-100. (250 nM final concentration) in the presence and absence of the isolated thromboplastin peptide (1 μM) or control peptide (1 μM), at 37° C. Aliquots (100 μl) were removed at the start and at various intervals up to 180 min and assayed by means of the one-stage prothrombin time assay. The residual activity of thromboplastin measured in the samples was compared to the initial activity, at time zero, and percentage inhibition calculated.

Computer Modelling of the Interaction of KRAD-14 with Thromboplastin (Residues 58–66)

A computer based search of the entire primary sequence of apolipoprotein B-100 was carried out to determine the concentration of positive residues and lysine residues within the protein sequence. In addition information gathered using "Peptide structure" program (GCC, University of Wisconsin, USA) produced clues about the span and structure of these domains.

KRAD-14 sequence was constructed using the Alchemy III and energy minimisation carried out, until the energy gradient (the difference in energy between two iterations) was below 0.01. In order to explain a possible mode of interaction between KRAD-14 and the complementary domain within thromboplastin (residues 58–66) the KRAD-14 peptide, essentially, an α-helix, was positioned at an approximate angle of 20° [12] to thromboplastin (residue 58–66), hence indicating the interacting amino acids.

The structure of KRAD-98 was predicted to be a four-helix bundle as determined by the Threader program [22]. The helices and the turns within the structure were determined and the structure was then modelled using the Alchemy III program.

The results are discussed below with reference to the figures which provide the following data.

FIG. 1 shows the time-course assay of the inhibition of thromboplastin by KRAD-14, KRAD-98 and reconstituted apolipoprotein B-100.

Three 1 ml samples containing recombinant thromboplastin (10 U/ml) were mixed with 500 nM KRAD-14 (solid square), 500 nM KRAD-98 (open square) or 500 nM apolipoprotein B-110 (triangle), reconstituted as described before. The concentrations used are equivalent to that of apolipoprotein B-100 in normal plasma. 100 μl of the each sample was removed immediately and assayed for thromboplastin activity, by means of the one-stage prothrombin time assay. The rest of the samples were incubated at 37° C. and further 100 μl samples were removed at intervals up to 120 min and measured as before. The thromboplastin activity was calculated from a standard curve prepared previously and the percentage inhibition was calculated as 100×(Initial activity/Residual activity)/Initial activity. The curves are typical of data from four sets of experiments.

Figure 2:
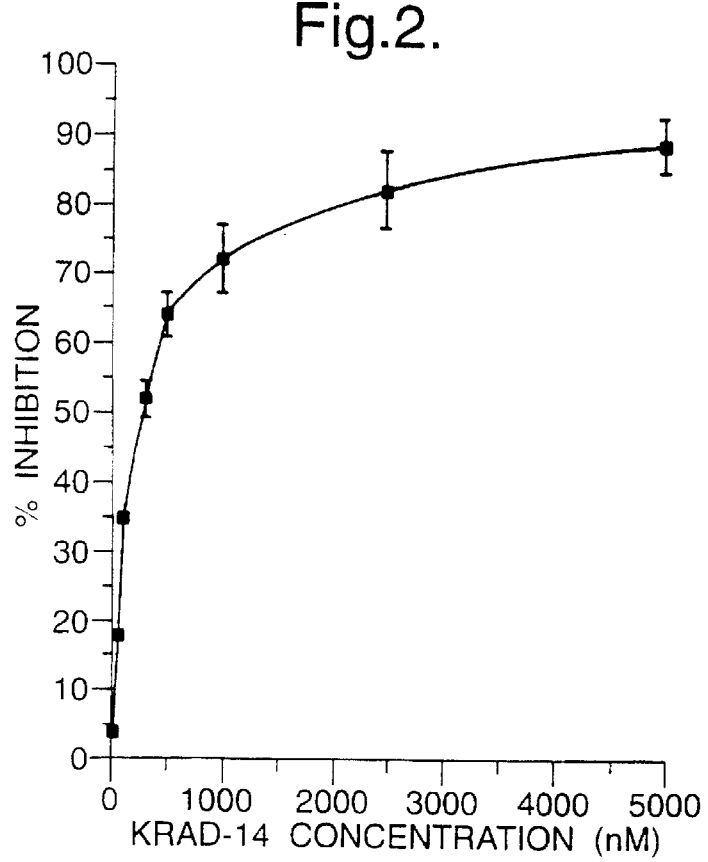
FIG. 2. Effect of the KRAD-14 concentration on thromboplastin inhibition.

FIG. 2 shows the effect of the KRAD-14 concentration on thromboplastin inhibition.

Aliquots of recombinant thromboplastin were incubated, at 37° C. with a KRAD-14 at concentration range 10–5000 nM (final concentration) for 1 min prior to assaying using the one-stage prothrombin time assay. The percentage inhibition was calculated as 100×(Initial activity/Residual activity)/Initial activity. The experiment was performed in triplicate.

Figure 3B:
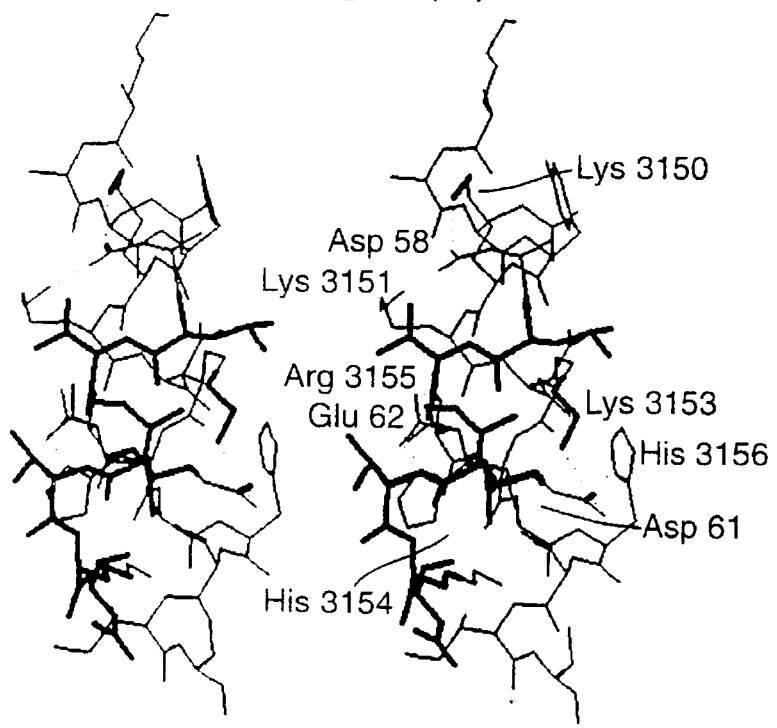
FIG. 3b. Stereo model of the interaction of KRAD-14 with thromboplastin fragment (58–66).
Figure 3A:
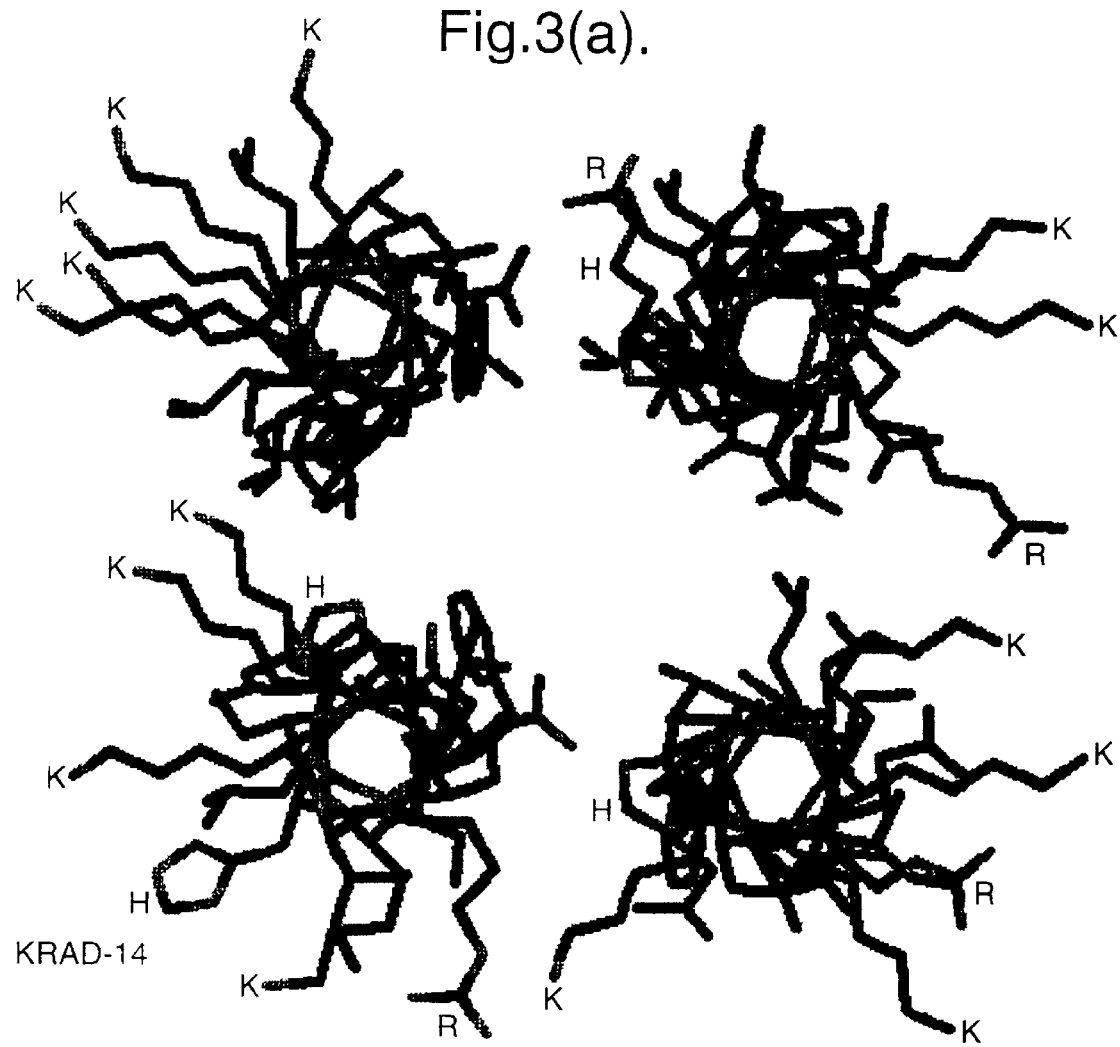
FIG. 3a. Top view of the four-helix bundle model of KRAD-98 peptide.

FIG. 3a Top view of the four-helix bundle model of KRAD-98 peptide.

KRAD-98 sequence (apolipoprotein B-100 residues 3121–3217) was constructed as a four-helix bundle using Alchemy III. The amino acids involved in the turns were omitted for clarity. The positively charged amino acids, lysine (K), arginine (R) and histidine (H) residues were highlighted to demonstrate the positive envelope surrounding the domain. KRAD-14 sequence has been indicated.

FIG. 3b shows a stereo model of the interaction of KRAD-14 with thromboplastin fragment (58–66).

Samples of thromboplastin (10 U/ml) were incubated with synthetic KRAD-14 concentration ranging 1–100 μM (final concentration) prior to assaying using the one-stage prothrombin time assay. The percentage inhibition was calculated as 100×(Initial activity/Residual activity)/Initial activity. The experiment was performed in triplicate.

KRAD-14 sequences were constructed using the Alchemy III and energy minimisation carried out, until the energy gradient was below 0.01. In order to explain a possible mode of interaction between KRAD-14 and the complementary domain within thromboplastin (residues 58–66) the KRAD-14 peptide, essentially, an α-helix, was positioned at an approximate angle of 20° to thromboplastin (residue 58–66), hence indicating the interacting amino acids.

Figure 3C:
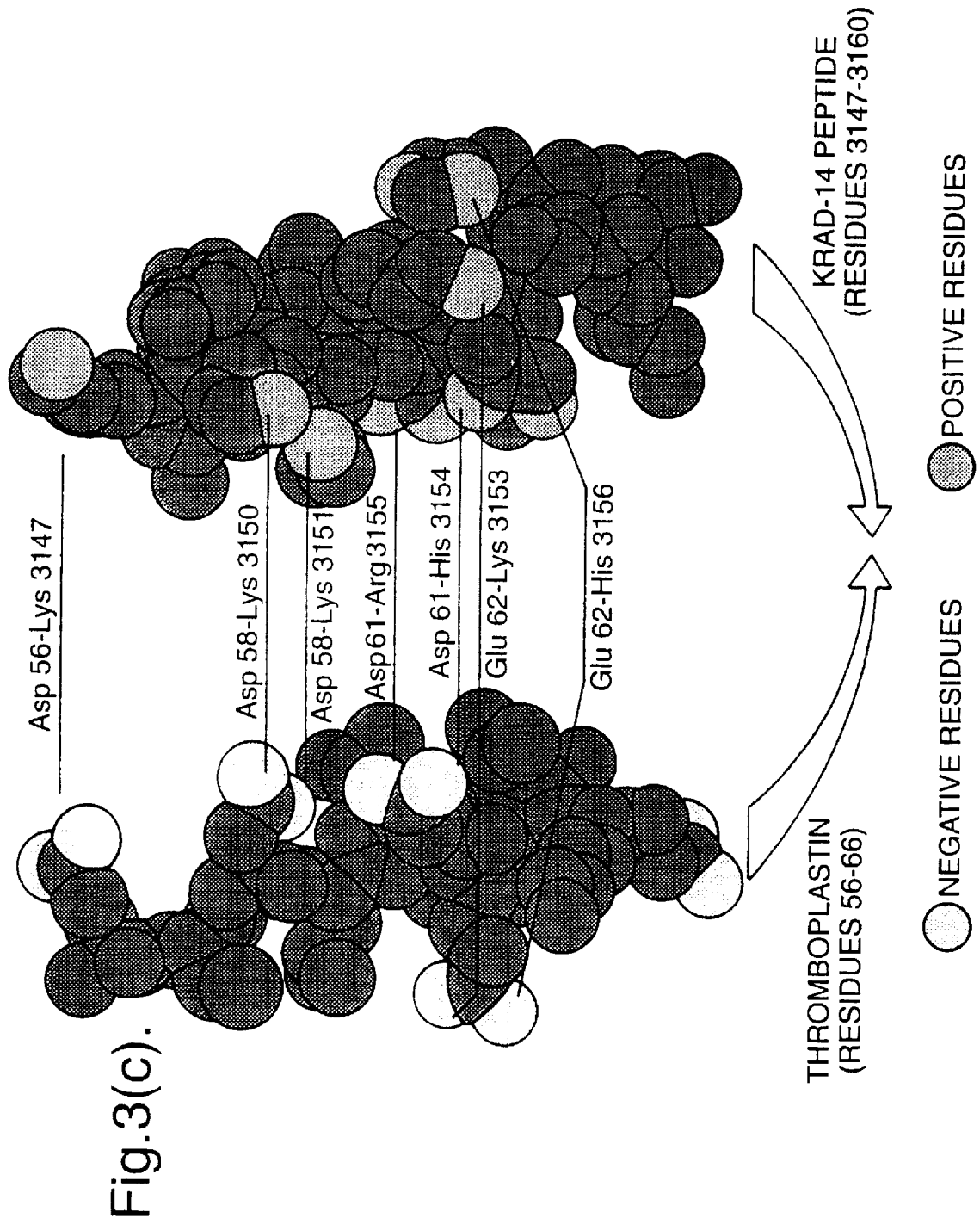
FIG. 3c. Space-filling model of KRAD-14 peptide and thromboplastin fragment (56–66) indicating the interacting amino acids.

FIG. 3c. Space-filling model of KRAD-14 peptide and thromboplastin fragment (56–66) indicating the interacting amino acids.

KRAD-14 sequence were constructed using Alchemy III and energy minimisation carried out, until the energy gradient was below 0.01. In order to explain a possible mode of interaction between KRAD-14 peptide and the complementary domain within thromboplastin (residues 56–66) the KRAD-14 peptide, essentially, an alpha-helix, was positioned at an approximate angle of 20° to thromboplastin (residue 56–66), hence indicating the interacting amino acids. The interacting positive and negative residues were marked and the two sequence turned by 90° in opposite directions to reveal the interacting-charged pockets. In the model, aspartate 56 (thromboplastin) interacts with lysine 3147 (apo B-100), aspartate 58 (thromboplastin) interacts with lysine 3150 and 3151 (apo B-100), aspartate 61 (thromboplastin) interacts with arginine 3155 and histidine 3154 (apo B-100), glutamate 62 (thromboplastin) interacts with lysine 3153 and histidine 3156 (apo B-100).

Figure 4:
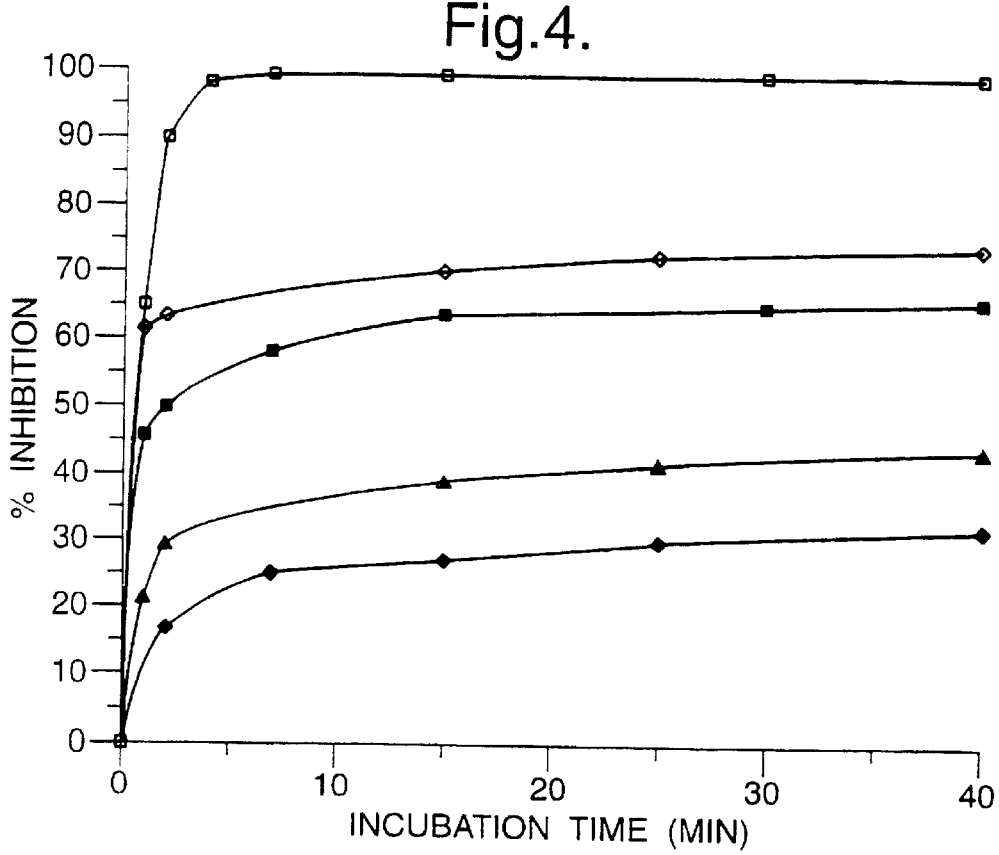
FIG. 4. Effect of the KRAD-14 peptide concentration on inhibition of thromboplastin.

FIG. 4. Effect of the KRAD-14 peptide concentration on inhibition of thromboplastin.

Aliquots (1 ml) of recombinant thromboplastin (100 nM) were incubated at 37° C. with a KRAD-14 peptide at concentration range 50 (♦), 100 (▼), 200 (■), 300 (◊) and 500 nM (□) (final concentration). 100 µl of the each sample was removed immediately and assayed for thromboplastin activity, by means of the one-stage prothrombin time assay. The rest of the samples were incubated at 37° C. and further 100 µl samples were removed at intervals up to 40 min and measured. The percentage inhibition was calculated as 100× (Initial activity-Residual activity)/Initial activity. The data were obtained from 3 separate experiments.

Figure 5:
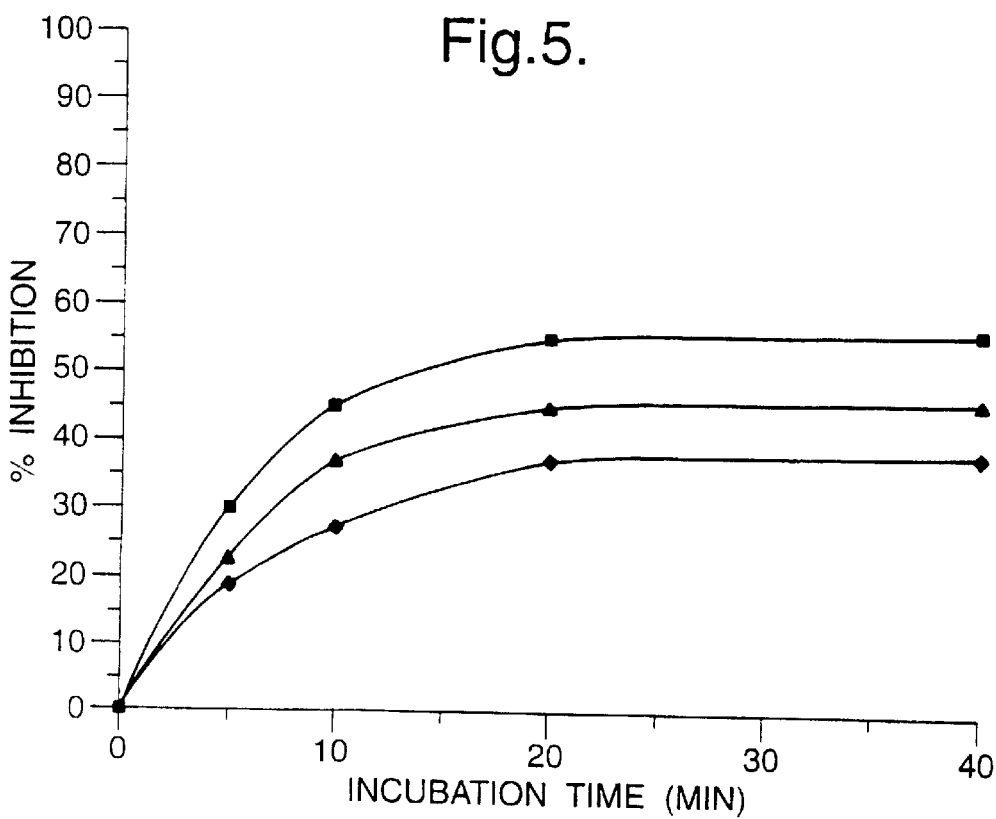
FIG. 5. Time-course assay of the inhibition of the procoagulant activity of factor X by KRAD-14 peptide.

FIG. 5. Time-course assay of the inhibition of the procoagulant activity of factor X by KRAD-14 peptide Three 1 ml samples containing recombinant KRAD-14 peptide (20 (♦), 40 (▼) and 80 (■) nM) were mixed with factor Xa (100 nM). 100 µl of the each sample was removed immediately and assayed for factor Xa activity by addition to factor Xa-deficient plasma in the presence of $CaCl_2$ (25 mM) and measuring the clotting time. The rest of the samples were incubated at 37° C. and further 100 µl samples were removed at intervals up to 40 min and measured as before. The activity was measured against a standard curve and the percentage inhibition calculated against the initial factor Xa activity. The curves are typical of data from 3 separate experiments.

Figure 6:
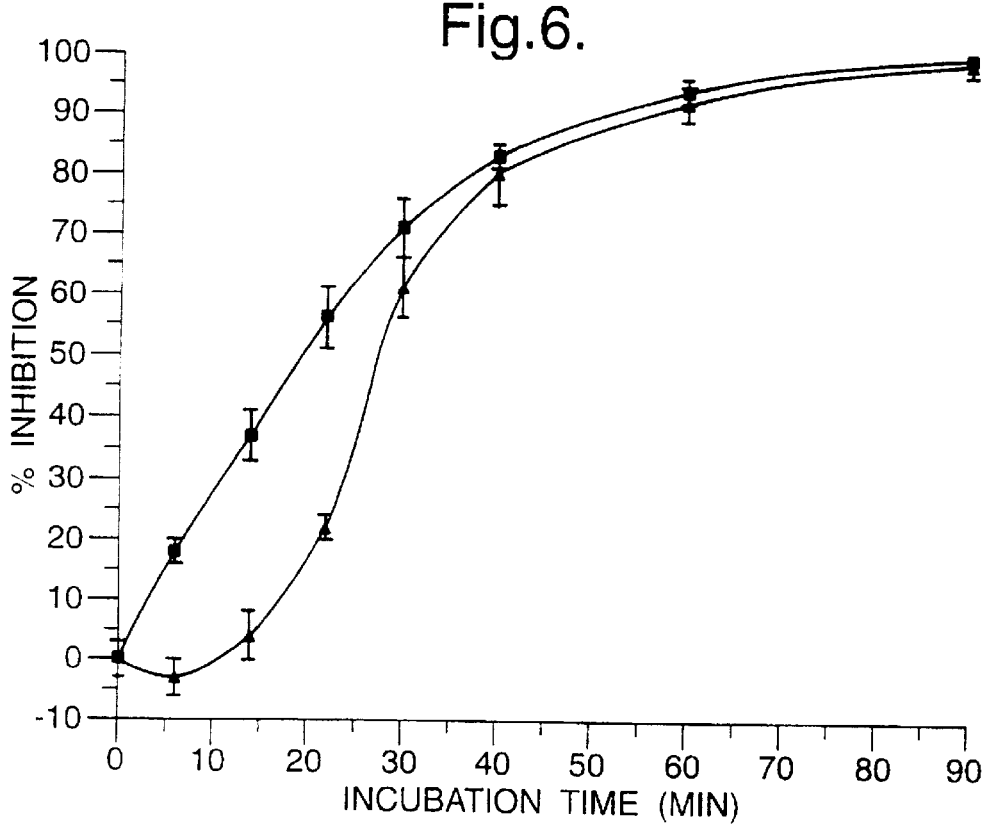
FIG. 6. Time-course assay of the inhibition of the procoagulant activity of factor V by KRAD-14 peptide.

FIG. 6. Time-course assay of the inhibition of the procoagulant activity of factor V by KRAD-14 peptide.

Three 1 ml samples containing recombinant KRAD-14 peptide (20 (♦) 40 (▼) and 80 (■) nM) were mixed with factor V (1 µM). 100 µl of the each sample was removed immediately and assayed for factor Xa activity by addition to factor V-deficient plasma, pre-activated by incubation (2 min) with thromboplastin (200 nM) in the presence of $CaCl_2$ (25 mM), and measuring the clotting time. The rest of the samples were incubated at 37° C. and further 100 µl samples were removed at intervals up to 40 min and measured as before. The activity was measured against a standard curve and the percentage inhibition calculated against the initial factor V activity. The curves are typical of data from 3 separate experiments.

Figure 7:
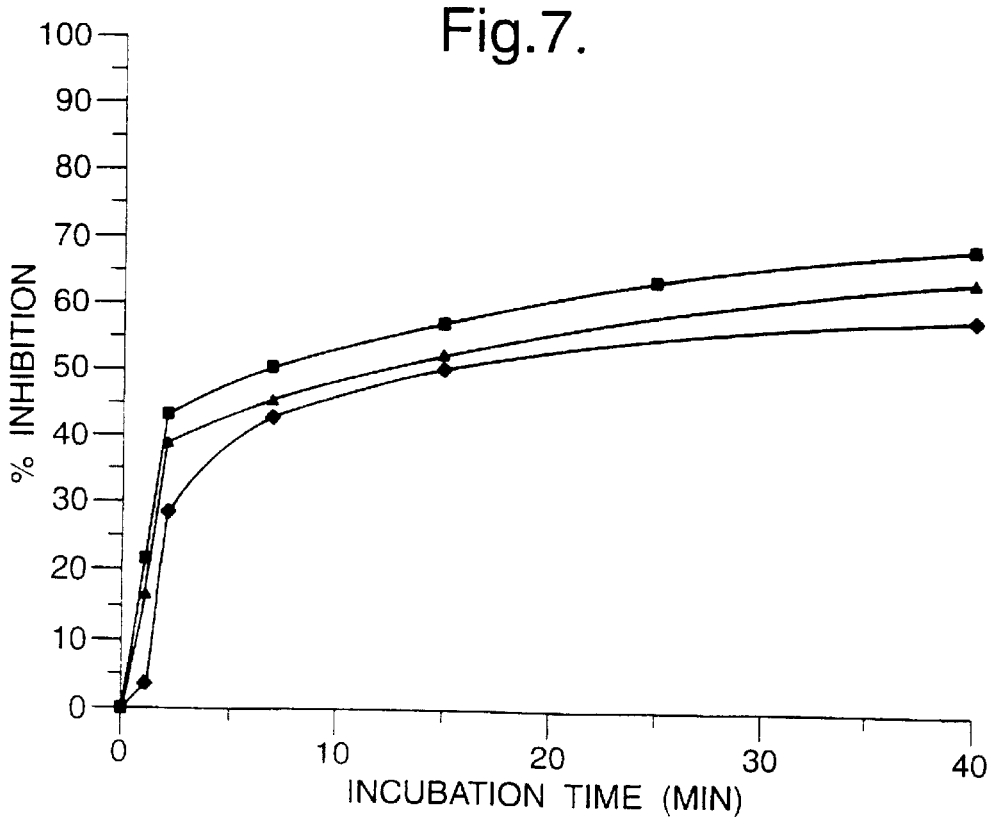
FIG. 7. Influence of the peptide 58–66, on the interaction and inhibition of thromboplastin by apo B-100.

FIG. 7. Influence of the peptide 58–66, on the interaction and inhibition of thromboplastin by apo B-100

Samples of thromboplastin (100 nM) were incubated with reconstituted apo B-100 (250 nM final concentration) in the presence (■) and absence (▼) of the isolated thromboplastin peptide (1 µM), at 37° C. Aliquots (100 µM) were removed at the start (time zero) and at various intervals up to 180 min and assayed by means of the one-stage prothrombin time assay. The data presented are representative of 5 independent experiments.

Results

Preparation of Recombinant Peptides

On propagation only the cells containing the control plasmid or the plasmid-insert survived. The procedure used allowed only the unidirectional insertion of the KRAD-14, KRAD-98, control peptides and thromboplastin (58–66) fragments. Western blotting of KRAD-14 and KRAD-98 peptides revealed bands of biotinylated protein with molecular weights of 15 KDa (thromboplastin fragment 58–66), 18 KDa (KRAD-14) and 27 KDa (KRAD-98) which agree with theoretical molecular weight calculated for the fusion peptides. The control chloramphenicol acetyltransferase sample contained a protein with a molecular weight of 40 KDa (control protein). In addition, fainter bands of biotinylated proteins (22.5 KDa) were detected, which are endogenous to the strains of *E. coli*.

Effect of KRAD-14 and KRAD-98 on Thromboplastin Activity

The data from the one-stage prothrombin assay and the two-stage amidolytic assay were comparable and the percentage inhibition was calculated from the data generated using both methods. In the first experiment, samples of thromboplastin (100 nM) were incubated with KRAD-14 peptide (500 nM), KRAD-98 peptide (500 nM), reconstituted apolipoprotein B-100 (500 nM) or each of the control peptides (500 nM) at 37° C. Samples were removed immediately and at intervals up to 120 min and assayed for thromboplastin activity KRAD-14 inhibited the procoagulant activity of thromboplastin by 98% following 4 min incubation. KRAD-98 exhibited a 95% inhibition of thromboplastin after 45 min incubation. On the other hand, neither the control 15 mer apolipoprotein B-100 (fragment 3358–3372) peptide nor the chloramphenicol acetyltransferase control protein had any detectable effect on thromboplastin. Reconstituted apolipoprotein B-100 also inhibited the procoagulant activity of thromboplastin (>95%) after 90 min incubation. The inclusion of calcium-free plasma during the incubations prior to assaying, did not significantly affect the ability of KRAD-14 or KRAD-98 peptide (500 nM) to inhibit thromboplastin activity.

On incubation of thromboplastin with KRAD-14 peptide, the procoagulant activity was inhibited rapidly, reaching 90% at 2 min and a maximum of 98% within 4 min (FIG. 1). On the other hand, both KRAD-98 attained an inhibition level of >90% following a minimum of 40 min incubation, and reconstituted apolipoprotein B-100 took 70 min to reach inhibition levels of >90%.

Preincubation of plasma with thromboplastin resulted in a slightly shorter clotting time and hence a higher apparent thromboplastin activity. However, the presence of plasma did not affect the ability of the KRAD-14 to inhibit thromboplastin activity and following 2 min incubation 74% inhibition was detected. Similarly, KRAD-98 exhibited 95% inhibition following 40 min incubation.

The incubation of thromboplastin with a range of KRAD-14 peptide concentrations (10–500 nM) demonstrated that the inhibition is concentration dependent and exhaustible (FIG. 2). However, KRAD-14 was effective at concentration as low as 50 nM. Moreover, the inhibition was unstable and completely disappeared after approximately 8 min following reconstitution. This deterioration was partially stabilised by adjusting the pH and addition of 5 nM bovine serum albumin as a stabiliser. However, the inhibitory effect deteriorated rapidly, completely disappearing after 15 min, following reconstitution.

The preincubation of thromboplastin (100 nM) with a range of KRAD-14 peptide concentrations (1–5000 nM) for 1 min at 37° C., demonstrated that the inhibition is concentration dependent and exhaustible (FIG. 4) ($Kd_{app}$=3.7×10$^{-8}$). However KRAD-14 peptide was effective at concentrations as low as 50 nM. The synthetic KRAD-14 peptide was also inhibitory towards thromboplastin with similar effectiveness as the recombinant peptide.

Reconstitution of delipidated recombinant thromboplastin in phosphatidylcholine reduced the activity of the sample by 200 fold. However, the presence of KRAD-14 (500 nM) or KRAD-98 (500 nM) peptides inhibited this activity by over 99 and 85% respectively (Table 1). This indicates that the inhibitory effect does not solely arise from the interaction of the KRAD-14 peptide with the negatively charged phosphatidylserine associated with thromboplastin.

TABLE 1

Inhibition of thromboplastin, reconstituted in phosphatidylcholine, by KRAD-14, KRAD-98 peptides and reconstituted apolipoprotein B-100.

| Sample | Procoagulant Activity | % Inhibition |
|---|---|---|
| Distilled water (4.70 U/ml) | 0.06 | — |
| APO B-100 control peptide (3358–3372) (4.68 U/ml) | 0.06 | 0.4 |
| Reverse KRAD-14 (4.68 U/ml) | 0.08 | 0.4 |
| Proline-rich KRAD-14 (4.71 U/ml) | 0.04 | −0.2 |
| Scrambled KRAD-14 (4.61 U/ml) | 0.08 | 1.9 |
| Recombinant KRAD-14 peptide (0.05 U/ml) | 0.04 | 99 |
| Recombinant KRAD-98 peptide (0.71 U/ml) | 0.04 | 85 |
| Reconstituted apo B-100 (1.79 U/ml) | 0.05 | 62 |

Recombinant thromboplastin was delipidated to remove phosphatidylserine and other lipids and reconstituted at 1 mg/ml with phosphatidylcholine (1 mg/ml). Four 1 ml samples were incubated with either 500 nM KRAD-14 peptide, 500 nM KRAD-98 peptide, 500 nM reconstituted apolipoprotein B-100 or each of the four control peptides (500 nM) or distilled water at 37° C. for 30 min, prior to assay. The % Inhibition was calculated against the control. The data were obtained from 3 separate experiments.

Effect of KRAD-14 on Thrombin and Factor Xa and Factor V Activity

The KRAD-14 peptide (500 nM) did not affect either the clotting ability or the amidolytic proteolytic activity of thrombin (100 nM). Neither control peptide had any significant effect on thrombin activity. The peptide (500 nM) did not affect the amidolytic activity of factor Xa. However, some inhibition of coagulation was observed upon preincubation of KRAD-14 with either factor Xa (100 nM) (Kdapp=2.75×10$^{-7}$) (FIG. 5) or factor V (1 μM) (Kdapp=2.85×10$^{-7}$) (FIG. 6). The coagulation assays were carried out by incubating the KRAD-14 peptide with factor Xa or V respectively, at 37° C. for up to 60 min, prior to assaying in factor Xa deficient plasma or preactivated factor V deficient plasma. Neither control peptide had any effect on the factor Xa or V activities.

Investigation of the Effect of KRAD-14 on Activation and Activity of Factor VII

In order to assess whether the action of KRAD-14 peptide was directed to the proteolytic activity of factor VIIa/thromboplastin or the activation of factor VII by interaction with thromboplastin, first thromboplastin (200 nM) and factor VII (200 nM) were incubated for 10 min in the presence of 25 mM CaCl$_2$, prior to addition of EPIC peptide (500 nM) and a further 10 min incubation. In the second experiment thromboplastin, factor VII and factor Xa (100 nM) were pre-incubated for 10 min in the presence of 25 mM CaCl$_2$, prior to addition of KRAD-14 peptide and a further 10 min incubation. The samples were then assayed by addition to factor VII deficient plasma and measuring the clotting time. KRAD-14 peptide did not significantly affect the activity of factor VIIa (inhibition=12%+8). Conversely, it was able to inhibit the activation of the pro-enzyme (inhibition=74%+8) (Table 2). Neither control peptide had any measurable effect on factor VII/thromboplastin activity or factor VII activation.

TABLE 2

The influence of peptide 58–66 on the procoagulant activity of thromboplastin.

| Sample | Procoagulant Activity |
|---|---|
| Distilled water (6.70 U/ml) | 0.11 |
| Control peptide (6.75 U/ml) | 0.06 |
| Peptide 56–66 (7.45 U/ml) | 0.06 |

Three aliquots of thromboplastin (100 nM) were incubated for 5 min, with the isolated thromboplastin peptide (1 μM), control peptide (1 μM) or distilled water at 37° C. prior to assaying using the one-stage prothrombin time assay. The activity was calculated from a thromboplastin standard curve. The data were obtained from 3 separate experiments.

Effects of Thromboylastin (58–66) on Thromboylastin Activity and Inhibition

The isolated thromboplastin-derived peptide (58–66) had no endogenous procoagulant activity. The addition of the recombinant thromboplastin (1 μM) enhanced the procoagulant activity of thromboplastin (100 nM) while the control of peptide did not have any significant effect. Thromboplastin-peptide heterodimer exhibited a stronger procoagulant activity than the thromboplastin-thromboplastin homodimer. The presence of the thromboplastin peptide (1 μM) but not control peptide, also accelerated the rate of inhibition of thromboplastin activity (100 nM) by reconstituted apo B-100 (250 nM) (FIG. 7). The thromboplastin peptide heterodimer exhibited a faster rate of interaction with apo B-100.

Computer Modelling of the Interaction of KRAD-14 with Thromboplastin (residues 58–66)

The computer-based analysis of the entire apolipoprotein B-100 sequence revealed two distinct regions with a large proportion of positively charged amino acids. The sequences residues 3121–3217 (KRAD-98) and residues 3300–3400 are both within the receptor binding domain of apolipoprotein B-100. This is in agreement with published data [10–13]. The former domain is also especially rich in lysine residues. KRAD-98 was predicted to be a distinct four-helix bundle domain within apolipoprotein B100 (FIG. 1). In this model the domain is surrounded by positively charged amino acids, particularly lysines, which make the domain hydrophilic and exposed. The highest concentration of lysine residues was within the amino acid regions 3147–3160 (KRAD-14). In order to explain a possible mode of interaction between KRAD-14 and the complementary domain within thromboplastin (residues 58–66) the KRAD-14 sequence were constructed and positioned at an approximate angle of 20° [12] to thromboplastin (residue 58–66) (FIG. 3b). In this interaction, the lysine and histidine residues within KRAD-14 form pockets of positive charge around the negatively charged aspartate and glutamate amino acids within thromboplastin (residues 58–66).

In this model, the lysine 3150 and lysine 3151 of apo B-100, interact with aspartate 58 of thromboplastin, lysine 3153 and histidine 3156 of apo B-100, interact with aspartate 61 of thromboplastin and histidine 3154 and arginine 3155 of apo B-100, interact with glutamate 62 of thromboplastin. In addition, lysine 3147 of apo B-100, may interact with asparate 56 of thromboplastin.

The involvement of the thromboplastin sequence (58–66) and particularly aspartate 58 in binding and activity of factor VII has been demonstrated recently [13]. Hence, it is possible that, the interaction of KRAD-14 and apolipoprotein B-100 with this domain disrupts the ability of thromboplastin to bind factor VII, effectively inhibiting the procoagulant activity.

Discussion

We previously reported that the interaction of thromboplastin with apolipoprotein B-100 occurs in at least two sites [7]. Thus, while the first site involves the attainment of a more hydrophobic configuration or the formation of hydrophobic interactions and occurs within 20 min of incubation, the evidence suggests that the second interaction, involves negatively charged residues and positive free amino groups, occurring over a longer period of time (up to 60 min). Furthermore, a possible apolipoprotein B-binding site on thromboplastin, due to its similarity to apolipoprotein B-100 binding domain within LDL-receptor protein, was indicated. In addition, it was reported that the interaction and inhibition of thromboplastin by apolipoprotein B is dependent on lysine residue within the primary sequence of the latter [Ettelaie et al unpublished data].

On the other hand, the presence of cationic amino acid per se was not sufficient for the inhibition since the cationic peptide from apolipoprotein B-100 (fragment 3358–3372) had no effect. The ability of KRAD-98 to inhibit thromboplastin activity in the same manner as native apo B-100 suggests that the inhibitory potential of apo B-100 arises from this domain (residues 3121–3217). This domain is also believed to be involved in the interaction of apo B-100 with the cellular receptor for LDL [10], hence enforcing our previous suggestion that the interaction between apo B-100 and thromboplastin is essentially similar in nature to that between apo B-100 and its receptor [7]. In addition, previously, we suggested that the interaction and inhibition of thromboplastin by apolipoprotein B-100 occurs via a two-step mechanism [7], the first step of which involves the non-specific hydrophobic interaction of these two proteins. The absence of the lag time preceding the rise in inhibition, as observed with apo B-100 enforces this mechanism.

By attempting to match a complementary sequence to those found in thromboplastin (residues 58–66) and LDL-receptor protein (residues 283–291), we were able to select a sequence within apolipoprotein B-100 that fulfilled the criteria required. By cloning and expressing the peptide as a fusion protein, we were able to purify and assay any potential of this peptide sequence. The lysine-rich apolipoprotein B-100 derived (KRAD-14) peptide was altered in two amino acids to increase the hydrophilic property of the peptide without affecting its secondary structure, significantly.

The peptide sequence was shown to be an efficient inhibitor of thromboplastin. In addition, the rate of inhibition observed was much faster than that observed with either LDL or apolipoprotein B-100 [4–6,7,11]. This may be due to the immense size of apolipoprotein B and LDL since the protein has to manoeuvre into correct orientation for correct interaction with thromboplastin. Alternatively, the presence of lipids may be a factor in the rate of association of the two proteins. Also the inhibition was more stable than that observed with thromboplastin pathway inhibitor (TFPI) [11].

Thromboplastin is structurally related to class two cytokine receptors [14]. Furthermore, the peptide ligands for such receptors are normally helical [15]. Therefore, we propose that KRAD-14 is a suitable ligand for thromboplastin the binding of which masks amino acids essential for binding to factor VII and hence procoagulant activity.

The ability of these peptides to inhibit thromboplastin activity, when reconstituted in phosphatidylcholine, indicate that the activity of the peptide arises from a direct interaction with thromboplastin rather than a non-specific association with the negatively charged phosphatidylserine molecules which tend to enhance thromboplastin activity [2,27].

The thromboplastin (58–66) peptide enhanced the procoagulant activity of thromboplastin by acting co-operatively, an effect similar to that observed from the dimerisation of thromboplastin [27,28]. In addition, the smaller size of the peptide allows a faster rate of binding. This faster rate of interaction was also observed when examining the interaction of apo B-100 with thromboplastin. Therefore, the inhibitory action of apo B-100 on the extrinsic pathway of inhibition arises from the action on thromboplastin via direct interaction involving the sequence residues 58–66 within thromboplastin [8] and may displace factor VII preventing its activation.

This work has identified the interacting site between apolipoprotein B-100 and thromboplastin which results in the inhibition of the procoagulant activity of the latter. It appears that the interactions mask amino acids essential for binding and activation of factor VII, particularly aspartate 58 [22,23], hence inhibiting the procoagulant activity.

From this work we conclude that the inhibitory action of KRAD-14 or apolipoprotein B-100 on the extrinsic pathway of inhibition arises from a direct action on thromboplastin via direct interaction [7], and is dissimilar to that of TFPI which is essentially a protease inhibitor [16]. The accelerated effect of KRAD-14, as compared to apolipoprotein B-100, as well as its size and ease of preparation, makes this a suitable potential agent in treatment of hypercoagulable conditions.

REFERENCES

1. Nemerson, Y., Pepke, D. Tissue factor accelerates the activation of coagulation factor VII:the role of a bifunctional coagulation cofactor. *Thromb. Res.* 51, 165–173 (1985).
2. Nemerson, Y. Tissue factor and haemostasis. *Blood* 71, 1–8 (1988).
3. Howell, R. M., Ettelaie, C. Inhibition of thromboplastin by serum fractions from various species. *Biochem. Soc. Trans.* 17, 576–577(1989) Abstract.
4. Howell, R. M., Ettelaie, C. The effect of barium sulphate adsorbable proteins on thromboplastin activity. *Biochem. Soc. Trans.* 18, 680–681 (1990) Abstract.
5. Ettelaie, C., Howell, R. M., Bruckdorfer, K. R. The effect of lipid peroxidation and lipolysis on the ability of lipoproteins to influence thromboplastin activity. *Biochim. Biophys. Acta* 1257, 25–30 (1995).
6. Ettelaie, C., Howell, R. M. The inhibition of thromboplastin by apolipoprotein B and the effect of various lipids. *Thromb. Res.* 68, 175–184(1992).
7. Ettelaie, C., James, N. J., Wilbourn, B., Adam, J. M., Naseem, K. M., Bruckdorfer, K. R. The mechanism of inhibition of factor III (thromboplastin) activity by apolipoprotein-100:Protein—protein interactions. *Arterosclerosis, Thrombosis and Vascular Biology* 16, In press (1996).
8. Mills, G. L., Lane, P. A., Weech, P. K. In *A Guidebook to Lipoprotein Technique*, eds. Burdon, R. H., Van Knippenberg, P. H., Vol. 14, Elsevier, London, New York (1984).
9. Sandset, P. M., Abildgaard, U., Pettersen, M. A sensitive assay of extrinsic coagulation pathway inhibitor in plasma and plasma fractions. *Thromb. Res.* 47, 389–400 (1987).
10. Goldstein, J. L., Brown, M. S. Receptor mediated endocytosis. *Annu. Rev. Cell Biol.* 1, 1–39 (1985).
11. Ettelaie, C., Wilbourn, B., Adam, J. M., James, N. J., Bruckdorfer, K. R Comparison of the inhibitory effects of TFPI and apolipoprotein B-100 on the procoagulant activity of thromboplastin Blood Coag. *Fibrinolysis* In press.
12. Chothia, C., Levitt, M., Richardson, D. Helix-to-helix packing in proteins. *J. Mol. Biol.* 145, 215–250 (1981).
13. Banner, D. W., D'Arcy, A., Chene, C., Winkler, F. K., Guha, A., Konigsberg, W. H., Nemerson, Y., Kirchhofer, D. The crystal structure of the complex of blood coagulation factor VIIa with soluble tissue factor *Nature* 380, 41–46 (1996).
14. Harlos, K., Martin, D. M. A., O'Brien, D. P., Jones, E. Y., Stuart, D. I., Polikarpov, I., Miller, A., Tuddenham, E. G. D., Boys, C. W. G. Crystal structure of the extracellular region of human tissue factor. *Nature* 370, 662–666 (1994).
15. Ruf, W., Schullek, J. R., Stone, M. J., Edgington, T. S. Mutational mapping of functional residues in tissue factor: identification of factor VII recognition determinants in both structural modules of the predicted cytokine homology domain. *Biochemistry* 33, 1565–1572.
16. Girard, T. S., Warren, L. A., Novotny, W. F., Likert, K. M., Brown, S. G., Miletich, J. P., Broze, G. J. Functional significance of the kunitz-type inhibitory domains of LACI *Nature* 338, 518–520 (1989).
17. Chou, P. Y., Fasman, G. D. Empirical predictions of protein conformation. *Annu. Rev. Biochem.* 47, 251, 1978
18. Garnier, J., Osguthorpe, D. J., Robson, B. Analysis of the accuracy and implications of simple methods for predicting the secondary structure of globular proteins. *J. Mol. Biol.* 120, 97, 1978
19. Ettelaie, C., Wilbourn, B., Adam, J. M., James, N. J., Bruckdorfer, K. R Comparison of the inhibitory effects of TFPI and apolipoprotein B-100 on the procoagulant activity of tissue factor. Blood Coag. Fibrinolysis 7, P11, 1996 (abstr)
20. Ettelaie, C., Howell, R. M. The inhibition of tissue factor by apolipoprotein B and the effect of various lipids. Thromb. Res. 68, 175, 1992
21. Ettelaie, C., James, N. J., Wilbourn, B., Adam, J. M., Naseem, K. M., Bruckdorfer, K. R. The mechanism of inhibition of factor III (tissue factor) activity by apolipoprotein-100:Protein—protein interactions. Arteriosclerosis, Thrombosis and Vascular Biology 16, 639, 1996
22. Jones, D., Taylor, W. R., Thornton, J. M. A new approach to protein fold recognition. Nature, 358, 86, 1992
23. Milne, R., Theolis, R., Maurice, R., Pease, R., Weech, P., Rassar, E., Fruchart, J-C., Scott, J., Marcel, Y. The use of monoclonal antibodies to localize the low density lipoprotein receptor-binding domain of apolipoprotein B-100. J. Biol. Chem. 264, 19754, 1989
24. Lawn, A., Scott, J. A cross-species comparison of apolipoprotein B domain that binds to the LDL receptor. J. Lipid Res. 31, 1109, 1990
25. Chan, L. Apolipoprotein B, the major protein component of triglyceride-rich and low density lipoproteins. J. Biol. Chem. 267, 25621, 1992
26. Olsson, U., Camejo, G., Hurt-Camejo, E., Elfsber, K., Wiklund, O., Bondjers, G. Possible functional interactions of apolipoprotein B-100 segments that associate with cell proteoglycans and the apo B/E receptor. 17, 149, 1997.
27. Bach, R., Gentry, R., Nemerson, Y. Factor VII binding to tissue factor in reconstituted phospholipid vesicles: Induction of cooperativety by phosphatidylserine. Biochemistry 25, 4007, 1986
28. Harlos, K., Martin, D. M. A., O'Brien, D. P., Jones, E. Y., Stuart, D. I., Polikarpov, I., Miller, A., Tuddenham, E. G. D., Boys, C. W. G. Crystal structure of the extracellular region of human tissue factor. Nature 370, 662, 1994

SEQUENCE INFORMATION

Amino acid sequence of human apolipoprotein B-100.

KRAD-14 (amino acids 3147–3160) is underlined. The positively charged sequence within amino acids 3300–3400 (amino acids 3358–3367) is also underlined. Two cysteine residues that can be used to join the first and second peptides of the invention via a disulphide bond are also underlined.

```
  1 EEEMLENVSL VCPKDATRFK HLRKYTYNYE AESSSGVPGT ADSRSATRIN

51 CKVELEVPQL CSFILKTSQC TLKEVYGFNP EGKALLKKTK NSEEFAAAMS

101 RYELKLAIPE GKQVFLYPEK DEPTYILNIK RGIISALLVP PETEEAKQVL

151 FLDTVYGNCS THFTVKTRKG NVATEISTER DLGQCDRFKP IRTGISPLAL

201 IKGMTRPLST LISSSQSCQY TLDAKRKHVA EAICKEQHLF LPFSYKNKYG

251 MVAQVTQTLK LEDTPKINSR FFGEGTKKMG LAFESTKSTS PPKQAEAVLK

301 TLQELKKLTI SEQNIQRANL FNKLVTELRG LSDEAVTSLL PQLIEVSSPI

351 TLQALVQCGQ PQCSTHILQW LKRVHANPLL IDVVTYLVAL IPEPSAQQLR
```

-continued

```
 401 EIFNMARDQR SRATLYALSH AVNNYHKTNP TGTQELLDIA NYLMEQIQDD
 451 CTGDEDYTYL ILRVIGNMGQ TMEQLTPELK SSILKCVQST KPSLMIQKAA
 501 IQALRKMEPK DKDQEVLLQT FLDDASPGDK RLAAYLMLMR SPSQADINKI
 551 VQILPWEQNE QVKNFVASHI ANILNSEELD IQDLKKLVKE VLKESQLPTV
 601 MDFRKFSRNY QLYKSVSLPS LDPASAKIEG NLIFDPNNYL PKESMLKTTL
 651 TAFGFASADL IEIGLEGKGF EPTLEALFGK QGFFPDSVNK ALYWVNGQVP
 701 DGVSKVLVDH FGYTKDDKHE QDMVNGIMLS VEKLIKDLKS KEVPEARAYL
 751 RILGEELGFA SLHDLQLLGK LLLMGARTLQ GIPQMIGEVI RKGSKNDFFL
 801 HYIFMENAFE LPTGAGLQLQ ISSSGVIAPG AKAGVKLEVA NMQAELVAKP
 851 SVSVEFVTNM GIIIPDFARS GVQMNTNFFH ESGLEAHVAL KAGKLKFIIP
 901 SPKRPVKLLS GGNTLHLVST TKTEVIPPLI ENRQSWSVCK QVFPGLNYCT
 951 SGAYSNASST DSASYYPLTG DTRLELELRP TGEIEQYSVS ATYELQREDR
1001 ALVDTLKFVT QAEGAKQTEA TMTFKYNRQS MTLSSEVQIP DFDVDLGTIL
1051 RVNDESTEGK TSYRLTLDIQ NKKITEVALM GHLSCDTKEE RKIKGVISIP
1101 RLQAEARSEI LAHWSPAKLL LQMDSSATAY GSTVSKRVAW HYDEEKIEFE
1151 WNTGTNVDTK KMTSNFPVDL SDYPKSLHMY ANRLLDHRVP QTDMTFRHVG
1201 SKLIVAMSSW LQKASGSLPY TQTLQDHLNS LKEFNLQNMG LPDFHIPENL
1251 FLKSDGRVKY TLNKNSLKIE IPLPFGGKSS RDLKMLETVR TPALHFKSVG
1301 FHLPSREFQV PTFTIPKLYQ LQVPLLGVLD LSTNVYSNLY NWSASYSGGN
1351 TSTDHFSLRA RYHMKADSVV DLLSYNVQGS GETTYDHKNT FTLSCDGSLR
1401 HKFLDSNIKF SHVEKLGNNP VSKGLLIFDA SSSWGPQMSA SVHLDSKKKQ
1451 HLFVKEVKID GQFRVSSFYA KGTYGLSCQR DPNTGRLNGE SNLRFNSSYL
1501 QGTNQITGRY EDGTLSLTST SDLQSGIIKN TASLKYENYE LTLKSDTNGK
1551 YKNFATSNKM DMTFSKQNAL LRSEYQADYE SLRFFSLLSG SLNSHGLELN
1601 ADILGTDKIN SGAHKATLRI GQDGISTSAT TNLKCSLLVL ENELNAELGL
1651 SGASMKLTTN GRFREHNAKF SLDGKAALTE LSLGSAYQAM ILGVDSKNIF
1701 NFKVSQEGLK LSNDMMGSYA EMKFDHTNSL NIAGLSLDFS SKLDNIYSSD
1751 KFYKQTVNLQ LQPYSLVTTL NSDLKYNALD LTNNGKLRLE PLKLHVAGNL
1801 KGAYQNNEIK HIYAISSAAL SASYKADTVA KVQGVEFSHR LNTDIAGLAS
1851 AIDMSTNYNS DSLHFSNVFR SVMAPFTMTI DAHTNGNGKL ALWGEHTGQL
1901 YSKFLLKAEP LAFTFSHDYK GSTSHHLVSR KSISAALEHK VSALLTPAEQ
1951 TGTWKLKTQF NNNEYSQDLD AYNTKDKIGV ELTGRTLADL TLLDSPIKVP
2001 LLLSEPINII DALEMRDAVE KPQEFTIVAF VKYDKNQDVH SINLPFFETL
2051 QEYFERNRQT IIVVLENVQR NLKHINIDQF VRKYRAALGK LPQQANDYLN
2101 SFNWERQVSH AKEKLTALTK KYRITENDIQ IALDDAKINF NEKLSQLQTY
2151 MIQFDQYIKD SYDLHDLKIA IANIIDEIIE KLKSLDEHYH IRVNLVKTIH
2201 DLHLFIENID FNKSGSSTAS WIQNVDTKYQ IRIQIQEKLQ QLKRHIQNID
2251 IQHLAGKLKQ HIEAIDVRVL LDQLGTTISF ERINDVLEHV KHFVINLIGD
2301 FEVAEKINAF RAKVHELIER YEVDQQIQVL MDKLVELAHQ YKLKETIQKL
2351 SNVLQQVKIK DYFEKLVGFT DDAVKKLNEL SFKTFIEDVN KFLDMLIKKL
```

```
2401 KSFDYHQFVD ETNDKIREVT QRLNGEIQAL ELPQKAEALK LFLEETKATV
2451 AVYLESLQDT KITLIINWLQ EALSSASLAH MKAKFRETLE DTRDRMYQMD
2501 IQQELQRYLS LVGQVYSTLV TYISDWWTLA AKNLTDFAEQ YSIQDWAKRM
2551 KALVEQGFTV PEIKTILGTM PAFEVSLQAL QKATFQTPDF IVPLTDLRIP
2601 SVQINFKDLK NIKIPSRFST PEFTILNTFH IPSFTIDFVE MKVKIIRTID
2651 QMLNSELQWP VPDIYLRDLK VEDIPLARIT LPDFRLPEIA IPEFIIPTLN
2701 LNDFQVPDLH IPEFQLPHIS HTIEVPTFGK LYSILKIQSP LFTLDANADI
2751 GNGTTSANEA GIAASITAKG ESKLEVLNFD FQANAQLSNP KINPLALKES
2801 VKFSSKYLRT EHGSEMLFFG NAIEGKSNTV ASLHTEKNTL ELSNGVIVKI
2851 NNQLTLDSNT KYFHKLNIPK LDFSSQADLR NEIKTLLKAG HIAWTSSGKG
2901 SWKWACPRFS DEGTHESQIS FTIEGPLTSF GLSNKINSKH LRVNQNLVYE
2951 SGSLNFSKLE IQSQVDSQHV GHSVLTAKGM ALFGEGKAEF TGRHDAHLNG
3001 KVIGTLKNSL FFSAQPFEIT ASTNNEGNLK VRFPLRLTGK IDFLNNYALF
3051 LSPSAQQASW QVSARFNQYK YNQNFSAGNN ENIMEAHVGI NGEANLDFLN
3101 IPLTIPEMRL PYTIITTPPL KDFSLWEKTG LKEFLKTTKQ SFDLSVKAQY
3151 KKNKHRHSIT NPLAVLCEFI SQSIKSFDRH FEKNRNNALD FVTKSYNETK
3201 IKFDKYKAEK SHDELPRTFQ IPGYTVPVVN VEVSPFTIEM SAFGYVFPKA
3251 VSMPSFSILG SDVRVPSYTL ILPSLELPVL HVPRNLKLSL PHFKELCTIS
3301 HIFIPAMGNI TYDFSFKSSV ITLNTNAELF NQSDIVAHLL SSSSSVIDAL
3351 QYKLEGTTRL TRKRGLKLAT ALSLSNKFVE GSHNSTVSLT TKNMEVSVAK
3401 TTKAEIPILR MNFKQELNGN TKSKPTVSSS MEFKYDFNSS MLYSTAKGAV
3451 DHKLSLESLT SYFSIESSTK GDVKGSVLSR EYSGTIASEA NTYLNSKSTR
3501 SSVKLQGTSK IDDIWNLEVK ENFAGEATLQ RIYSLWEHST KNHLQLEGLF
3551 FTNGEHTSKA TLELSPWQMS ALVQVHASQP SSFHDFPDLG QEVALNANTK
3601 NQKIRWKNEV RIHSGSFQSQ VELSNDQEKA HLDIAGSLEG HLRFLKNIIL
3651 PVYDKSLWDF LKLDVTTSIG RRQHLRVSTA FVYTKNPNGY SFSIPVKVLA
3701 DKFITPGLKL NDLNSVLVMP TFHVPFTDLQ VPSCKLDFRE IQIYKKLRTS
3751 SFALNLPTLP EVKFPEVDVL TKYSQPEDSL IPFFEITVPE SQLTVSQFTL
3801 PKSVSDGIAA LDLNAVANKI ADFELPTIIV PEQTIEIPSI KFSVPAGIVI
3851 PSFQALTARF EVDSPVYNAT WSASLKNKAD YVETVLDSTC SSTVQFLEYE
3901 LNVLGTHKIE DGTLASKTKG TLAHRDFSAE YEEDGKFEGL QEWEGKAHLN
3951 IKSPAFTDLH LRYQKDKKGI STSAASPAVG TVGMDMDEDD DFSKWNFYYS
4001 PQSSPDKKLT IFKTELRVRE SDEETQIKVN WEEEAASGLL TSLKDNVPKA
4051 TGVLYDYVNK YHWEHTGLTL REVSSKLRRN LQNNAEWVYQ GAIRQIDDID
4101 VRFQKAASGT TGTYQEWKDK AQNLYQELLT QEGQASFQGL KDNVFDGLVR
4151 VTQKFHMKVK HLIDSLIDFL NFPRFQFPGK PGIYTREELC TMFIREVGTV
4201 LSQVYSKVHN GSEILFSYFQ DLVITLPFEL RKHKLIDVIS MYRELLKDLS
4251 KEAQEVFKAI QSLKTTEVLR NLQDLLQFIF QLIEDNIKQL KEMKFTYLIN
4301 YIQDEINTIF NDYIPYVFKL LKENLCLNLH KFNEFIQNEL QEASQELQQI
4351 HQYIMALREE YFDPSIVGWT VKYYELEEKI VSLIKNLLVA LKDFHSEYIV
```

-continued

4401 SASNFTSQLS SQVEQFLHRN IQEYLSILTD PDGKGKEKIA ELSATAQEII

4451 KSQAIATKKI ISDYHQQFRY KLQDFSDQLS DYYEKFIAES KRLIDLSIQN

4501 YHTFLIYITE LLKKLQSTTV MNPYMKLAPG ELTIIL

What is claimed is:

1. A peptide whose amino acid sequence is $Z^1$—K—A—Q—$X^1$—K—K—N—K—H—R—H—S—$X^2$—T—$Z^2$ (SEQ ID NO:1)

where:
- $X^1$ represents S or Y,
- $X^2$ represents T or I,
- $Z^1$ represents the N terminus of the peptide, or from 1 to 47 amino acids, and
- $Z^2$ represents the C terminus of the peptide, a terminal amide group, or from 1 to 77 amino acids;

or a peptide whose sequence differs from the sequence of the peptide of SEQ ID NO:1 by up to 15% by virtue of internal deletions, insertions or substitutions;

said peptide possessing 0.5 fold or more the anti-coagulant activity of apolipoprotein B-100 (apoB-100); with the proviso that the sequence of said peptide is not the sequence of amino acids 3120–3159 of apoB-100.

2. A peptide whose amino acid sequence is $Z^1$—K—A—Q—$X^1$—K—K—N—K—H—R—H—S—$X^2$—T—$Z^2$ (SEQ ID NO:1)

where:
- $X^1$ represents S or Y,
- $X^2$ represents T or I,
- $Z^1$ represents the N terminus of the peptide, or from 1 to 47 amino acids,
- $Z^2$ represents the C terminus of the peptide, a terminal amide group, or from 1 to 77 amino acids;
- or a peptide whose sequence differs from the sequence of the peptide of SEQ ID NO:1 by up to 15% by virtue of internal deletions, insertions or substitutions;
  - said peptide possessing 0.5 fold or more the anti-coagulant activity of apolipoprotein B-100 (apoB-100);
  - wherein, when $X^1$ is Y and $X^2$ is I, $Z^1$ represents 20 or less amino acids.

3. A peptide comprising the amino acid sequence $Z^1$—K—A—Q—$X^1$—K—K—N—K—H—R—H—S—$X^2$—T—$Z^2$ (SEQ ID NO:1)

$Z^1$—Q—$X^1$—K—K—N—K—H—R—$Z^2$ (SEQ ID NO:2)

$Z^1$—A—Q—$X^1$—K—K—N—K—H—$Z^2$ (SEQ ID NO:3)

$Z^1$—A—Q—$X^1$—K—K—N—K—H—R—$Z^2$ (SEQ ID NO:4)

$Z^1$—Q—$X^1$—K—K—N—K—H—R—H—$Z^2$ (SEQ ID NO:5)

$Z^1$—A—Q—$X^1$—K—K—N—K—H—R—H—$Z^2$ (SEQ ID NO:6)

$Z^1$—Q—$X^1$—K—K—N—K—H—R—H—S—$Z^2$ (SEQ ID NO:7)

$Z^1$—A—Q—$X^1$—K—K—N—K—H—R—H—S—$Z^2$ (SEQ ID NO:8)

$Z^1$—K—A—Q—$X^1$—K—K—N—K—H—R—H—S—$Z^2$ (SEQ ID NO:9)

$Z^1$—A—Q—$X^1$—K—K—N—K—H—R—H—S—$X^2$—$Z^2$ (SEQ ID NO:10)

$Z^1$—K—A—Q—$X^1$—K—K—N—K—H—R—H—S—$X^2$—$Z^2$ (SEQ ID NO:11)

or a sequence of any one of SEQ ID Nos. 1 to 11 comprising up to 4 amino acid substitutions;
where:
- $X^1$ represents S or Y,
- $X^2$ represents T or I,
- $Z^1$ represents the N terminus of the peptide, or from 1 to 20 amino acids,
- $Z^2$ represents the C terminus of the peptide, a terminal amide group, or from 1 to 20 amino acids;
  - said peptide possessing 0.5 fold or more the anti-coagulant activity of apolipoprotein B-100 (apoB-100).

4. A peptide comprising the amino acid sequence $Z^1$KKNK$Z^2$;

where:
- $Z^1$ represents the N terminus of the peptide, or from 1 to 20 amino acids,
- $Z^2$ represents the C terminus of the peptide, a terminal amide group, or from 1 to 20 amino acids;
  - said peptide possessing 0.5 fold or more the anti-coagulant activity of apolipoprotein B-100 (apoB-100).

5. A peptide whose amino acid sequence is

K—A—Q—$X^1$—K—K—N—K—H—R—H—S—$X^2$—T (SEQ ID NO:1)

where:
- $X^1$ represents S or Y,
- $X^2$ represents T or I.

6. A peptide whose amino acid sequence is the sequence of amino acids 21 to 118 of SEQ ID NO:12.

7. The peptide of claim 1 wherein $Z^1$ is up to 20 and $Z^2$ is up to 10; $Z^1$ is up to 20 and $Z^2$ is up to 5; $Z^1$ is up to 5 and $Z^2$ is up to 10; or $Z^1$ is up to 5 and $Z^2$ is up to 20.

8. The peptide of claim 2 wherein $Z^1$ is up to 20 and $Z^2$ is up to 10; $Z^1$ is up to 20 and $Z^2$ is up to 5, Z is up to 5 and $Z^2$ is up to 10; or $Z^1$ is up to 5 and $Z^2$ is up to 20.

9. The peptide of claim 3 wherein $Z^1$ is up to 20 and $Z^2$ is up to 10; $Z^1$ is up to 20 and $Z^2$ is up to 5; $Z^1$ is up to 5 and $Z^2$ is up to 10; or $Z^1$ is up to 5 and $Z^2$ is up to 20.

10. The peptide of claim 4 wherein $Z^1$ is up to 20 and $Z^2$ is up to 10; $Z^1$ is up to 20 and $Z^2$ is up to 5; $Z^1$ is up to 5 and $Z^2$ is up to 10; or $z^1$ is up to 5 and $Z^2$ is up to 20.

11. The peptide of claim 1 which has at least the anti-coagulant activity of apoB-100.

12. The peptide of claim 2 which has at least the anti-coagulant activity of apoB-100.

13. The peptide of claim 3 which has at least the anti-coagulant activity of apoB-100.

14. The peptide of claim 4 which has at least the anti-coagulant activity of apoB-100.

15. A pharmaceutical composition comprising a peptide whose amino acid sequence is $Z^1$—K—A—Q—$X^1$—K—K—N—K—H—R—H—S—$X^2$—T—$Z^2$ (SEQ ID NO:1)

where:
- $X^1$ represents S or Y,
- $X^2$ represents T or I,
- $Z^1$ represents the N terminus of the peptide, or from 1 to 47 amino acids, and
- $Z^2$ represents the C terminus of the peptide, a terminal amide group, or from 1 to 77 amino acids;
- or a peptide whose sequence differs from the sequence of the peptide of SEQ ID NO:1 by up to 15% by virtue of internal deletions, insertions or substitutions;
  - said peptide possessing 0.5 fold or more the anti-coagulant activity of apolipoprotein B-100 (apoB-100);
  - with the proviso that the sequence of said peptide is not the sequence of amino acids 3120–3159 of apoB-100;
- and a pharmaceutically acceptable diluent or carrier.

16. A pharmaceutical composition a peptide whose amino acid sequence is $Z^1$—K—A—Q—$X^1$—K—K—N—K—H—R—H—S—$X^2$—T—$Z^2$ (SEQ ID NO:1)

where:
- $X^1$ represents S or Y,
- $X^2$ represents T or I,
- $Z^1$ represents the N terminus of the peptide, or from 1 to 47 amino acids,
- $Z^2$ represents the C terminus of the peptide, a terminal amide group, or from 1 to 77 amino acids;
- or a peptide whose sequence differs from the sequence of the peptide of SEQ ID NO:1 by up to 15% by virtue of internal deletions, insertions or substitutions;

comprising said peptide possessing 0.5 fold or more the anti-coagulant activity of apolipoprotein B-100 (apoB-100);
wherein, when $X^1$ is Y and $X^2$ is I, $Z^1$ represents 20 or less amino acids;
and a pharmaceutically acceptable diluent or carrier.

17. A pharmaceutical composition comprising a peptide comprising the amino acid sequence $Z^1$—K—A—Q—$X^1$—K—K—N—K—H—R—H—S—$X^2$—T—$Z^2$ (SEQ ID NO:1)

$Z^1$—Q—$X^1$—K—K—N—K—H—R—$Z^2$ (SEQ ID NO:2)

$Z^1$—A—Q—$X^1$—K—K—N—K—H—$Z^2$ (SEQ ID NO:3)

$Z^1$—A—Q—$X^1$—K—K—N—K—H—$Z^2$ (SEQ ID NO:4)

$Z^1$—Q—$X^1$—K—K—N—K—H—R—H—$Z^2$ (SEQ ID NO:5)

$Z^1$—A—Q—$X^1$—K—K—N—K—H—R—H—$Z^2$ (SEQ ID NO:6)

$Z^1$—Q—$X^1$—K—K—N—K—H—R—H—S—$Z^2$ (SEQ ID NO:7)

$Z^1$—A—Q—$X^1$—K—K—N—K—H—R—H—S—$Z^2$ (SEQ ID NO:8)

$Z^1$—K—A—Q—$X^1$—K—K—N—K—H—R—H—S—$Z^2$ (SEQ ID NO:9)

$Z^1$—A—Q—$X^1$—K—K—N—K—H—R—H—S—$X^2$—$Z^2$ (SEQ ID NO:10)

$Z^1$—K—A—Q—$X^1$—K—K—N—K—H—R—H—S—$X^2$—$Z^2$ (SEQ ID NO:11)

or a sequence of any one of SEQ ID Nos. 1 to 11 comprising up to 4 amino acid substitutions;
where:
$X^1$ represents S or Y,
$X^2$ represents T or I,
$Z^1$ represents the N terminus of the peptide, or from 1 to 20 amino acids,
$Z^2$ represents the C terminus of the peptide, a terminal amide group, or from 1 to 20 amino acids;
said peptide possessing 0.5 fold or more the anti-coagulant activity of apolipoprotein B-100 (apoB-100);
and a pharmaceutically acceptable diluent or carrier.

18. A pharmaceutical composition comprising a peptide comprising the amino acid sequence $Z^1$KKNK$Z^2$;
where:
$Z^1$ represents the N terminus of the peptide, or from 1 to 20 amino acids,
$Z^2$ represents the C terminus of the peptide, a terminal amide group, or from 1 to 20 amino acids;
said peptide possessing 0.5 fold or more the anti-coagulant activity of apolipoprotein B-100 (apoB-100);
and a pharmaceutically acceptable diluent or carrier.

19. A pharmaceutical composition comprising a peptide whose amino acid sequence is

K—A—Q—$X^1$—K—K—N—K—H—R—H—S—$X^2$—T (SEQ ID NO:1)

where:
$X^1$ represents S or Y,
$X^2$ represents T or I;
and a pharmaceutically acceptable diluent or carrier.

20. A pharmaceutical composition comprising a peptide whose amino acid sequence is the sequence of amino acids 21 to 118 of SEQ ID NO:12; and a pharmaceutically acceptable diluent or carrier.

21. A composition comprising a compound of claim 1 and a matrix metalloproteinase inhibitor.

22. A composition comprising a compound of claim 2 and a matrix metalloproteinase inhibitor.

23. A composition comprising a compound of claim 3 and a matrix metalloproteinase inhibitor.

24. A composition comprising a compound of claim 4 and a matrix metalloproteinase inhibitor.

25. A composition comprising a compound of claim 5 and a matrix metalloproteinase inhibitor.

26. A composition comprising a compound of claim 6 and a matrix metalloproteinase inhibitor.

27. A method of treatment of a patient who requires therapy for a condition requiring inhibition of a thromboplastin-related process which comprises administering to said patient an effective amount of a peptide whose amino acid sequence is $Z^1$—K—A—Q—$X^1$—K—K—N—K—H—R—H—S—$X^2$—T—$Z^2$ (SEQ ID NO:1)

where:
$X^1$ represents S or Y,
$X^2$ represents T or I,
$Z^1$ represents the N terminus of the peptide, or from 1 to 47 amino acids, and
$Z^2$ represents the C terminus of the peptide, a terminal amide group, or from 1 to 77 amino acids;
or a peptide whose sequence differs from the sequence of the peptide of SEQ ID NO:1 by up to 15% by virtue of internal deletions, insertions or substitutions;
said peptide possessing 0.5 fold or more the anti-coagulant activity of apolipoprotein B-100 (apoB-100);
with the proviso that the sequence of said peptide is not the sequence of amino acids 3120–3159 of apoB-100.

28. A method of treatment of a patient who requires therapy for a condition requiring inhibition of a thromboplastin-related process which comprises administering to said patient an effective amount of a peptide whose amino acid sequence is $Z^1$—K—A—Q—$X^1$—K—K—N—K—H—R—H—S—$X^2$—T—$Z^2$ (SEQ ID NO:1)

where:
$X^1$ represents S or Y,
$X^2$ represents T or I,
$Z^1$ represents the N terminus of the peptide, or from 1 to 47 amino acids,
$Z^2$ represents the C terminus of the peptide, a terminal amide group, or from 1 to 77 amino acids;
or a peptide whose sequence differs from the sequence of the peptide of SEQ ID NO:1 by up to 15% by virtue of internal deletions, insertions or substitutions;
said peptide possessing 0.5 fold or more the anti-coagulant activity of apolipoprotein B-100 (apoB-100);
wherein, when $X^1$ is Y and $X^2$ is I, $Z^1$ represents 20 or less amino acids.

29. A method of treatment of a patient who requires therapy for a condition requiring inhibition of a thromboplastin-related process which comprises administering to said patient an effective amount of a peptide comprising the amino acid sequence

```
Z¹-K-A-Q-X¹-K-K-N-K-H-R-H-S-X²-T-Z²    (SEQ ID NO:1)
Z¹-Q-X¹-K-K-N-K-H-R-Z²                  (SEQ ID NO:2)
Z¹-A-Q-X¹-K-K-N-K-H-Z²                  (SEQ ID NO:3)
Z¹-A-Q-X¹-K-K-N-K-H-R-Z²                (SEQ ID NO:4)
Z¹-Q-X¹-K-K-N-K-H-R-H-Z²                (SEQ ID NO:5)
Z¹-A-Q-X¹-K-K-N-K-H-R-H-Z²              (SEQ ID NO:6)
Z¹-Q-X¹-K-K-N-K-H-R-H-S-Z²              (SEQ ID NO:7)
Z¹-A-Q-X¹-K-K-N-K-H-R-H-S-Z²            (SEQ ID NO:8)
Z¹-K-A-Q-X¹-K-K-N-K-H-R-H-S-Z²          (SEQ ID NO:9)
Z¹-A-Q-X¹-K-K-N-K-H-R-H-S-X²-Z²         (SEQ ID NO:10)
Z¹-K-A-Q-X¹-K-K-N-K-H-R-H-S-X²-Z²       (SEQ ID NO:11)
``` or a sequence of any one of SEQ ID NOs. 1 to 11 comprising up to 4 amino acid substitutions;
where:
$X^1$ represents S or Y,
$X^2$ represents T or I,
$Z^1$ represents the N terminus of the peptide, or from 1 to 20 amino acids,
$Z^2$ represents the C terminus of the peptide, a terminal amide group, or from 1 to 20 amino acids;
said peptide possessing 0.5 fold or more the anti-coagulant activity of apolipoprotein B-100 (apoB-100).

30.

UNITED STATES PATENT AND TRADEMARK OFFICE
CERTIFICATE OF CORRECTION

PATENT NO. : 6,444,644 B1
DATED : September 3, 2002
INVENTOR(S) : Bruckdorfer et al.

It is certified that error appears in the above-identified patent and that said Letters Patent is hereby corrected as shown below:

Title page,
Item [56], References Cited, OTHER PUBLICATIONS, insert the following:
-- Radford, T (3/29/1997), The Guardian; "Micro-dose Medicines hit the right spot."; page A40 *
       Sandset et al (1987) Thromb. Res. 47: 389-400 * --.

Signed and Sealed this

Twenty-second Day of March, 2005

JON W. DUDAS
*Director of the United States Patent and Trademark Office*

SEQUENCE LISTING (1) GENERAL INFORMATION:

(iii) NUMBER OF SEQUENCES: 27

(2) INFORMATION FOR SEQ ID NO: 1:

(i) SEQUENCE CHARACTERISTICS:
      (A) LENGTH: 14 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION:4
      (D) OTHER INFORMATION:/note= "Xaa represents Ser or Tyr"

(ix) FEATURE:
      (A) NAME/KEY: Modified-site
      (B) LOCATION:13
      (D) OTHER INFORMATION:/note= "Xaa represents Thr or Ile"

(xi) SEQUENCE DESCRIPTION: SEQ ID NO: 1:

Lys Ala Gln Xaa Lys Lys Asn Lys His Arg His Ser Xaa Thr
1         5          10

(2) INFORMATION FOR SEQ ID NO: 2:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION:2
      (D) OTHER INFORMATION:/note= "Xaa is Ser or Tyr"

(xi) SEQUENCE DESCRIPTION: SEQ ID NO: 2:

Gln Xaa Lys Lys Asn Lys His Arg
1         5

(2) INFORMATION FOR SEQ ID NO: 3:

(i) SEQUENCE CHARACTERISTICS:
      (A) LENGTH: 8 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION:3
      (D) OTHER INFORMATION:/note= "Xaa can be Ser or Tyr"

(xi) SEQUENCE DESCRIPTION: SEQ ID NO: 3:

Ala Gln Xaa Lys Lys Asn Lys His
1               5

(2) INFORMATION FOR SEQ ID NO: 4:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION:3
         (D) OTHER INFORMATION:/note= "Xaa can be Ser or Tyr"

(xi) SEQUENCE DESCRIPTION: SEQ ID NO: 4:

Ala Gln Xaa Lys Lys Asn Lys His Arg
1               5

(2) INFORMATION FOR SEQ ID NO: 5:

(i) SEQUENCE CHARACTERISTICS:
         (A) LENGTH: 9 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION:2
         (D) OTHER INFORMATION:/note= "Xaa can be Ser or Tyr"

(xi) SEQUENCE DESCRIPTION: SEQ ID NO: 5:

Gln Xaa Lys Lys Asn Lys His Arg His
1               5

(2) INFORMATION FOR SEQ ID NO: 6:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide (ix) FEATURE:
         (A) NAME/KEY: Modified-site
         (B) LOCATION:3
         (D) OTHER INFORMATION:/note= "Xaa can be Ser or Tyr"

(xi) SEQUENCE DESCRIPTION: SEQ ID NO: 6:

Ala Gln Xaa Lys Lys Asn Lys His Arg His
1               5                   10

(2) INFORMATION FOR SEQ ID NO: 7:

(i) SEQUENCE CHARACTERISTICS:
         (A) LENGTH: 10 amino acids
         (B) TYPE: amino acid
         (C) STRANDEDNESS: single
         (D) TOPOLOGY: linear (ii) MOLECULE TYPE: peptide

```
        (ix) FEATURE:
             (A) NAME/KEY: Modified-site
             (B) LOCATION:2
             (D) OTHER INFORMATION:/note= "Xaa can be Ser or Tyr"

(xi) SEQUENCE DESCRIPTION: SEQ ID NO: 7:

Gln Xaa Lys Lys Asn Lys His Arg His Ser
1               5                   10

(2) INFORMATION FOR SEQ ID NO: 8:

(i) SEQUENCE CHARACTERISTICS:
             (A) LENGTH: 11 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Modified-site
             (B) LOCATION:3
             (D) OTHER INFORMATION:/note= "Xaa can be Ser or Tyr"

(xi) SEQUENCE DESCRIPTION: SEQ ID NO: 8:

Ala Gln Xaa Lys Lys Asn Lys His Arg His Ser
1               5                   10

(2) INFORMATION FOR SEQ ID NO: 9:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Modified-site
             (B) LOCATION:4
             (D) OTHER INFORMATION:/note= "Xaa can be Ser or Tyr"

(xi) SEQUENCE DESCRIPTION: SEQ ID NO: 9:

Lys Ala Gln Xaa Lys Lys Asn Lys His Arg His Ser
1               5                   10

(2) INFORMATION FOR SEQ ID NO: 10:

(i) SEQUENCE CHARACTERISTICS:
             (A) LENGTH: 12 amino acids
             (B) TYPE: amino acid
             (C) STRANDEDNESS: single
             (D) TOPOLOGY: linear (ii) MOLECULE TYPE: peptide (ix) FEATURE:
             (A) NAME/KEY: Modified-site
             (B) LOCATION:3
             (D) OTHER INFORMATION:/note= "Xaa can be Ser or Tyr"

(ix) FEATURE:
             (A) NAME/KEY: Modified-site
             (B) LOCATION:12
             (D) OTHER INFORMATION:/note= "Xaa can be Thr or Ile"

(xi) SEQUENCE DESCRIPTION: SEQ ID NO: 10:

Ala Gln Xaa Lys Lys Asn Lys His Arg His Ser Xaa
1               5                   10
```

(2) INFORMATION FOR SEQ ID NO: 11:

(i) SEQUENCE CHARACTERISTICS:
        (A) LENGTH: 13 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:4
        (D) OTHER INFORMATION:/note= "Xaa can be Ser or Tyr"

(ix) FEATURE:
        (A) NAME/KEY: Modified-site
        (B) LOCATION:13
        (D) OTHER INFORMATION:/note= "Xaa can be Thr or Ile"

(xi) SEQUENCE DESCRIPTION: SEQ ID NO: 11:

```
Lys Ala Gln Xaa Lys Lys Asn Lys His Arg His Ser Xaa
 1               5                  10
```

(2) INFORMATION FOR SEQ ID NO: 12:

(i) SEQUENCE CHARACTERISTICS:
        (A) LENGTH: 138 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 12:

```
Asn Ile Pro Leu Thr Ile Pro Glu Met Arg Leu Pro Tyr Thr Ile Ile
 1               5                  10                  15
Thr Thr Pro Pro Leu Lys Asp Glu Ser Leu Trp Glu Lys Thr Gly Leu
             20                  25                  30
Lys Glu Phe Leu Lys Thr Thr Lys Gln Ser Phe Asp Leu Ser Val Lys
             35                  40                  45
Ala Gln Tyr Lys Lys Asn Lys His Arg His Ser Ile Thr Asn Pro Leu
         50                  55                  60
Ala Val Leu Cys Glu Phe Ile Ser Gln Ser Ile Lys Ser Phe Asp Arg
65                  70                  75                  80
His Phe Glu Lys Asn Arg Asn Asn Ala Leu Asp Phe Val Thr Lys Ser
                 85                  90                  95
Tyr Asn Glu Thr Lys Ile Lys Phe Asp Lys Tyr Lys Ala Glu Lys Ser
                100                 105                 110
His Asp Glu Leu Pro Arg Thr Phe Gln Ile Pro Gly Tyr Thr Val Pro
            115                 120                 125
Val Val Asn Val Glu Val Ser Pro Phe Thr
            130                 135
```

(2) INFORMATION FOR SEQ ID NO: 13:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 13:

```
Arg Leu Thr Arg Lys Arg Gly Leu Lys Leu Ala Thr
1               5                   10
```

(2) INFORMATION FOR SEQ ID NO: 14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 14:

```
Asp Asp Asp Asp Lys
1               5
```

(2) INFORMATION FOR SEQ ID NO: 15:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 15:

```
Lys Lys Asn Lys
1
```

(2) INFORMATION FOR SEQ ID NO: 16:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "Xaa can be Ser or Tyr"

(xi) SEQUENCE DESCRIPTION: SEQ ID NO: 16:

```
Xaa Lys Lys Asn Lys His
1               5
```

(2) INFORMATION FOR SEQ ID NO: 17:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 17:

```
Thr Arg Leu Thr Arg Lys Arg Gly Leu Lys Leu Ala Thr Ala Leu
1               5                   10                  15
```

(2) INFORMATION FOR SEQ ID NO: 18:

(i) SEQUENCE CHARACTERISTICS:
        (A) LENGTH: 14 amino acids
        (B) TYPE: amino acid
        (C) STRANDEDNESS: single (D) TOPOLOGY: linear (ii) MOLECULE TYPE: peptide (xi) SEQUENCE DESCRIPTION: SEQ ID NO: 18:

Lys Ala Gln Ser Lys Lys Asn Lys His Arg His Ser Thr Thr
1               5                   10

(2) INFORMATION FOR SEQ ID NO: 19:

(i) SEQUENCE CHARACTERISTICS:
        (A) LENGTH: 14 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 19:

Lys Ala Gln Tyr Lys Lys Asn Lys His Arg His Ser Ile Thr
1               5                   10

(2) INFORMATION FOR SEQ ID NO: 20:

(i) SEQUENCE CHARACTERISTICS:
        (A) LENGTH: 55 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "Synthesised on (xi) SEQUENCE DESCRIPTION: SEQ ID NO: 20:

AGCTTTATAA AGCTCAGTCC AAAAAAAACA AACACCGTCA CTCCACCACC TAAGC          55

(2) INFORMATION FOR SEQ ID NO: 21:

(i) SEQUENCE CHARACTERISTICS:
        (A) LENGTH: 55 base pairs
        (B) TYPE: nucleic acid
        (C) STRANDEDNESS: both
        (D) TOPOLOGY: linear (ii) MOLECULE TYPE: other nucleic acid
        (A) DESCRIPTION: /desc = "Synthesised on (xi) SEQUENCE DESCRIPTION: SEQ ID NO: 21:

GGCCGCTTAG GTGGTGGAGT GACGGTGTTT GTTTTTTTTG GACTGAGCTT TATAA          55

(2) INFORMATION FOR SEQ ID NO: 22:

(i) SEQUENCE CHARACTERISTICS:
        (A) LENGTH: 9 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 22:

Asp Leu Thr Asp Glu Ile Val Lys Asp
1               5

(2) INFORMATION FOR SEQ ID NO: 23:

(i) SEQUENCE CHARACTERISTICS:
        (A) LENGTH: 40 base pairs
        (B) TYPE: nucleic acid

```
            (C) STRANDEDNESS: both
            (D) TOPOLOGY: linear (ii) MOLECULE TYPE: other nucleic acid
            (A) DESCRIPTION: /desc = "Synthesised on (xi) SEQUENCE DESCRIPTION: SEQ ID NO: 23:

AGCTTTATGA CCTGACCGAC GAAATCGTGA AAGACTAAGC                          40

(2) INFORMATION FOR SEQ ID NO: 24:

(i) SEQUENCE CHARACTERISTICS:
            (A) LENGTH: 40 base pairs
            (B) TYPE: nucleic acid
            (C) STRANDEDNESS: both
            (D) TOPOLOGY: linear (ii) MOLECULE TYPE: other nucleic acid
            (A) DESCRIPTION: /desc = "Synthesised on (xi) SEQUENCE DESCRIPTION: SEQ ID NO: 24:

GGCCGCTTAG TCTTTCACGA TTTCGTCGGT CAGGTCATAA                          40

(2) INFORMATION FOR SEQ ID NO: 25:

(i) SEQUENCE CHARACTERISTICS:
            (A) LENGTH: 4 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Modified-site
            (B) LOCATION:1
            (D) OTHER INFORMATION:/note= "Xaa is N-benzoyl-ile"

(ix) FEATURE:
            (A) NAME/KEY: Modified-site
            (B) LOCATION:4
            (D) OTHER INFORMATION:/note= "Xaa is arg-p-nitroanilide"

(xi) SEQUENCE DESCRIPTION: SEQ ID NO: 25:

Xaa Glu Gly Xaa
1

(2) INFORMATION FOR SEQ ID NO: 26:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO: 26:

Val Gln Gly Glu Glu Ser Asp Asn Lys
1               5

(2) INFORMATION FOR SEQ ID NO: 27:

(i) SEQUENCE CHARACTERISTICS:
            (A) LENGTH: 4536 amino acids
            (B) TYPE: amino acid
            (C) STRANDEDNESS: single
            (D) TOPOLOGY: linear (ii) MOLECULE TYPE: protein
```

-continued (xi) SEQUENCE DESCRIPTION: SEQ ID NO: 27:

| | | | | | | | | | | | | | | |
|---|---|---|---|---|---|---|---|---|---|---|---|---|---|---|
| Glu | Glu | Glu | Met | Leu | Glu | Asn | Val | Ser | Leu | Val | Cys | Pro | Lys | Asp | Ala |
| 1 | | | | 5 | | | | | 10 | | | | | 15 | |
| Thr | Arg | Phe | Lys | His | Leu | Arg | Lys | Tyr | Thr | Tyr | Asn | Tyr | Glu | Ala | Glu |
| | | | | 20 | | | | | 25 | | | | | 30 | |
| Ser | Ser | Ser | Gly | Val | Pro | Gly | Thr | Ala | Asp | Ser | Arg | Ser | Ala | Thr | Arg |
| | | | 35 | | | | | 40 | | | | | 45 | | |
| Ile | Asn | Cys | Lys | Val | Glu | Leu | Glu | Val | Pro | Gln | Leu | Cys | Ser | Phe | Ile |
| | 50 | | | | | 55 | | | | | 60 | | | | |
| Leu | Lys | Thr | Ser | Gln | Cys | Thr | Leu | Lys | Glu | Val | Tyr | Gly | Phe | Asn | Pro |
| 65 | | | | | 70 | | | | | 75 | | | | | 80 |
| Glu | Gly | Lys | Ala | Leu | Leu | Lys | Lys | Thr | Lys | Asn | Ser | Glu | Glu | Phe | Ala |
| | | | | 85 | | | | | 90 | | | | | 95 | |
| Ala | Ala | Met | Ser | Arg | Tyr | Glu | Leu | Lys | Leu | Ala | Ile | Pro | Glu | Gly | Lys |
| | | | | 100 | | | | | 105 | | | | | 110 | |
| Gln | Val | Phe | Leu | Tyr | Pro | Glu | Lys | Asp | Glu | Pro | Thr | Tyr | Ile | Leu | Asn |
| | | | 115 | | | | | 120 | | | | | 125 | | |
| Ile | Lys | Arg | Gly | Ile | Ile | Ser | Ala | Leu | Leu | Val | Pro | Pro | Glu | Thr | Glu |
| | 130 | | | | | 135 | | | | | 140 | | | | |
| Glu | Ala | Lys | Gln | Val | Leu | Phe | Leu | Asp | Thr | Val | Tyr | Gly | Asn | Cys | Ser |
| 145 | | | | | 150 | | | | | 155 | | | | | 160 |
| Thr | His | Phe | Thr | Val | Lys | Thr | Arg | Lys | Gly | Asn | Val | Ala | Thr | Glu | Ile |
| | | | | 165 | | | | | 170 | | | | | 175 | |
| Ser | Thr | Glu | Arg | Asp | Leu | Gly | Gln | Cys | Asp | Arg | Phe | Lys | Pro | Ile | Arg |
| | | | | 180 | | | | | 185 | | | | | 190 | |
| Thr | Gly | Ile | Ser | Pro | Leu | Ala | Leu | Ile | Lys | Gly | Met | Thr | Arg | Pro | Leu |
| | | | 195 | | | | | 200 | | | | | 205 | | |
| Ser | Thr | Leu | Ile | Ser | Ser | Gln | Ser | Cys | Gln | Tyr | Thr | Leu | Asp | Ala |
| | | 210 | | | | | 215 | | | | | 220 | | | |
| Lys | Arg | Lys | His | Val | Ala | Glu | Ala | Ile | Cys | Lys | Glu | Gln | His | Leu | Phe |
| 225 | | | | | 230 | | | | | 235 | | | | | 240 |
| Leu | Pro | Phe | Ser | Tyr | Lys | Asn | Lys | Tyr | Gly | Met | Val | Ala | Gln | Val | Thr |
| | | | | 245 | | | | | 250 | | | | | 255 | |
| Gln | Thr | Leu | Lys | Leu | Glu | Asp | Thr | Pro | Lys | Ile | Asn | Ser | Arg | Phe | Phe |
| | | | 260 | | | | | 265 | | | | | 270 | | |
| Gly | Glu | Gly | Thr | Lys | Lys | Met | Gly | Leu | Ala | Phe | Glu | Ser | Thr | Lys | Ser |
| | | | 275 | | | | | 280 | | | | | 285 | | |
| Thr | Ser | Pro | Pro | Lys | Gln | Ala | Glu | Ala | Val | Leu | Lys | Thr | Leu | Gln | Glu |
| | | 290 | | | | | 295 | | | | | 300 | | | |
| Leu | Lys | Lys | Leu | Thr | Ile | Ser | Glu | Gln | Asn | Ile | Gln | Arg | Ala | Asn | Leu |
| 305 | | | | | 310 | | | | | 315 | | | | | 320 |
| Phe | Asn | Lys | Leu | Val | Thr | Glu | Leu | Arg | Gly | Leu | Ser | Asp | Glu | Ala | Val |
| | | | | 325 | | | | | 330 | | | | | 335 | |
| Thr | Ser | Leu | Leu | Pro | Gln | Leu | Ile | Glu | Val | Ser | Ser | Pro | Ile | Thr | Leu |
| | | | 340 | | | | | 345 | | | | | 350 | | |
| Gln | Ala | Leu | Val | Gln | Cys | Gly | Gln | Pro | Gln | Cys | Ser | Thr | His | Ile | Leu |
| | | | 355 | | | | | 360 | | | | | 365 | | |
| Gln | Trp | Leu | Lys | Arg | Val | His | Ala | Asn | Pro | Leu | Leu | Ile | Asp | Val | Val |
| | | | 370 | | | | | 375 | | | | | 380 | | |
| Thr | Tyr | Leu | Val | Ala | Leu | Ile | Pro | Glu | Pro | Ser | Ala | Gln | Gln | Leu | Arg |
| 385 | | | | | 390 | | | | | 395 | | | | | 400 |
| Glu | Ile | Phe | Asn | Met | Ala | Arg | Asp | Gln | Arg | Ser | Arg | Ala | Thr | Leu | Tyr |
| | | | | 405 | | | | | 410 | | | | | 415 | |

```
Ala Leu Ser His Ala Val Asn Asn Tyr His Lys Thr Asn Pro Thr Gly
                420                 425                 430

Thr Gln Glu Leu Leu Asp Ile Ala Asn Tyr Leu Met Glu Gln Ile Gln
            435                 440                 445

Asp Asp Cys Thr Gly Asp Glu Asp Tyr Thr Tyr Leu Ile Leu Arg Val
        450                 455                 460

Ile Gly Asn Met Gly Gln Thr Met Glu Gln Leu Thr Pro Glu Leu Lys
465                 470                 475                 480

Ser Ser Ile Leu Lys Cys Val Gln Ser Thr Lys Pro Ser Leu Met Ile
                485                 490                 495

Gln Lys Ala Ala Ile Gln Ala Leu Arg Lys Met Glu Pro Lys Asp Lys
            500                 505                 510

Asp Gln Glu Val Leu Leu Gln Thr Phe Leu Asp Asp Ala Ser Pro Gly
        515                 520                 525

Asp Lys Arg Leu Ala Ala Tyr Leu Met Leu Met Arg Ser Pro Ser Gln
        530                 535                 540

Ala Asp Ile Asn Lys Ile Val Gln Ile Leu Pro Trp Glu Gln Asn Glu
545                 550                 555                 560

Gln Val Lys Asn Phe Val Ala Ser His Ile Ala Asn Ile Leu Asn Ser
                565                 570                 575

Glu Glu Leu Asp Ile Gln Asp Leu Lys Lys Leu Val Lys Glu Val Leu
            580                 585                 590

Lys Glu Ser Gln Leu Pro Thr Val Met Asp Phe Arg Lys Phe Ser Arg
        595                 600                 605

Asn Tyr Gln Leu Tyr Lys Ser Val Ser Leu Pro Ser Leu Asp Pro Ala
        610                 615                 620

Ser Ala Lys Ile Glu Gly Asn Leu Ile Phe Asp Pro Asn Asn Tyr Leu
625                 630                 635                 640

Pro Lys Glu Ser Met Leu Lys Thr Thr Leu Thr Ala Phe Gly Phe Ala
                645                 650                 655

Ser Ala Asp Leu Ile Glu Ile Gly Leu Glu Gly Lys Gly Phe Glu Pro
            660                 665                 670

Thr Leu Glu Ala Leu Phe Gly Lys Gln Gly Phe Phe Pro Asp Ser Val
        675                 680                 685

Asn Lys Ala Leu Tyr Trp Val Asn Gly Gln Val Pro Asp Gly Val Ser
        690                 695                 700

Lys Val Leu Val Asp His Phe Gly Tyr Thr Lys Asp Asp Lys His Glu
705                 710                 715                 720

Gln Asp Met Val Asn Gly Ile Met Leu Ser Val Glu Lys Leu Ile Lys
                725                 730                 735

Asp Leu Lys Ser Lys Glu Val Pro Glu Ala Arg Ala Tyr Leu Arg Ile
            740                 745                 750

Leu Gly Glu Glu Leu Gly Phe Ala Ser Leu His Asp Leu Gln Leu Leu
        755                 760                 765

Gly Lys Leu Leu Leu Met Gly Ala Arg Thr Leu Gln Gly Ile Pro Gln
        770                 775                 780

Met Ile Gly Glu Val Ile Arg Lys Gly Ser Lys Asn Asp Phe Phe Leu
785                 790                 795                 800

His Tyr Ile Phe Met Glu Asn Ala Phe Glu Leu Pro Thr Gly Ala Gly
                805                 810                 815

Leu Gln Leu Gln Ile Ser Ser Ser Gly Val Ile Ala Pro Gly Ala Lys
            820                 825                 830
```

-continued

```
Ala Gly Val Lys Leu Glu Val Ala Asn Met Gln Ala Glu Leu Val Ala
            835                 840                 845

Lys Pro Ser Val Ser Val Glu Phe Val Thr Asn Met Gly Ile Ile Ile
            850                 855                 860

Pro Asp Phe Ala Arg Ser Gly Val Gln Met Asn Thr Asn Phe Phe His
865                 870                 875                 880

Glu Ser Gly Leu Glu Ala His Val Ala Leu Lys Ala Gly Lys Leu Lys
                885                 890                 895

Phe Ile Ile Pro Ser Pro Lys Arg Pro Val Lys Leu Leu Ser Gly Gly
            900                 905                 910

Asn Thr Leu His Leu Val Ser Thr Thr Lys Thr Glu Val Ile Pro Pro
            915                 920                 925

Leu Ile Glu Asn Arg Gln Ser Trp Ser Val Cys Lys Gln Val Phe Pro
    930                 935                 940

Gly Leu Asn Tyr Cys Thr Ser Gly Ala Tyr Ser Asn Ala Ser Ser Thr
945                 950                 955                 960

Asp Ser Ala Ser Tyr Tyr Pro Leu Thr Gly Asp Thr Arg Leu Glu Leu
                965                 970                 975

Glu Leu Arg Pro Thr Gly Glu Ile Glu Gln Tyr Ser Val Ser Ala Thr
            980                 985                 990

Tyr Glu Leu Gln Arg Glu Asp Arg Ala Leu Val Asp Thr Leu Lys Phe
            995                 1000                1005

Val Thr Gln Ala Glu Gly Ala Lys Gln Thr Glu Ala Thr Met Thr Phe
    1010                1015                1020

Lys Tyr Asn Arg Gln Ser Met Thr Leu Ser Ser Glu Val Gln Ile Pro
1025                1030                1035                1040

Asp Phe Asp Val Asp Leu Gly Thr Ile Leu Arg Val Asn Asp Glu Ser
                1045                1050                1055

Thr Glu Gly Lys Thr Ser Tyr Arg Leu Thr Leu Asp Ile Gln Asn Lys
            1060                1065                1070

Lys Ile Thr Glu Val Ala Leu Met Gly His Leu Ser Cys Asp Thr Lys
    1075                1080                1085

Glu Glu Arg Lys Ile Lys Gly Val Ile Ser Ile Pro Arg Leu Gln Ala
    1090                1095                1100

Glu Ala Arg Ser Glu Ile Leu Ala His Trp Ser Pro Ala Lys Leu Leu
1105                1110                1115                1120

Leu Gln Met Asp Ser Ser Ala Thr Ala Tyr Gly Ser Thr Val Ser Lys
            1125                1130                1135

Arg Val Ala Trp His Tyr Asp Glu Glu Lys Ile Glu Phe Glu Trp Asn
            1140                1145                1150

Thr Gly Thr Asn Val Asp Thr Lys Lys Met Thr Ser Asn Phe Pro Val
            1155                1160                1165

Asp Leu Ser Asp Tyr Pro Lys Ser Leu His Met Tyr Ala Asn Arg Leu
    1170                1175                1180

Leu Asp His Arg Val Pro Gln Thr Asp Met Thr Phe Arg His Val Gly
1185                1190                1195                1200

Ser Lys Leu Ile Val Ala Met Ser Ser Trp Leu Gln Lys Ala Ser Gly
            1205                1210                1215

Ser Leu Pro Tyr Thr Gln Thr Leu Gln Asp His Leu Asn Ser Leu Lys
            1220                1225                1230

Glu Phe Asn Leu Gln Asn Met Gly Leu Pro Asp Phe His Ile Pro Glu
            1235                1240                1245

Asn Leu Phe Leu Lys Ser Asp Gly Arg Val Lys Tyr Thr Leu Asn Lys
```

-continued

```
            1250                1255                1260
Asn Ser Leu Lys Ile Glu Ile Pro Leu Pro Phe Gly Lys Ser Ser
1265                1270                1275                1280

Arg Asp Leu Lys Met Leu Glu Thr Val Arg Thr Pro Ala Leu His Phe
                1285                1290                1295

Lys Ser Val Gly Phe His Leu Pro Ser Arg Glu Phe Gln Val Pro Thr
            1300                1305                1310

Phe Thr Ile Pro Lys Leu Tyr Gln Leu Gln Val Pro Leu Leu Gly Val
        1315                1320                1325

Leu Asp Leu Ser Thr Asn Val Tyr Ser Asn Leu Tyr Asn Trp Ser Ala
    1330                1335                1340

Ser Tyr Ser Gly Gly Asn Thr Ser Thr Asp His Phe Ser Leu Arg Ala
1345                1350                1355                1360

Arg Tyr His Met Lys Ala Asp Ser Val Val Asp Leu Leu Ser Tyr Asn
                1365                1370                1375

Val Gln Gly Ser Gly Glu Thr Thr Tyr Asp His Lys Asn Thr Phe Thr
            1380                1385                1390

Leu Ser Cys Asp Gly Ser Leu Arg His Lys Phe Leu Asp Ser Asn Ile
        1395                1400                1405

Lys Phe Ser His Val Glu Lys Leu Gly Asn Asn Pro Val Ser Lys Gly
    1410                1415                1420

Leu Leu Ile Phe Asp Ala Ser Ser Ser Trp Gly Pro Gln Met Ser Ala
1425                1430                1435                1440

Ser Val His Leu Asp Ser Lys Lys Lys Gln His Leu Phe Val Lys Glu
                1445                1450                1455

Val Lys Ile Asp Gly Gln Phe Arg Val Ser Ser Phe Tyr Ala Lys Gly
            1460                1465                1470

Thr Tyr Gly Leu Ser Cys Gln Arg Asp Pro Asn Thr Gly Arg Leu Asn
        1475                1480                1485

Gly Glu Ser Asn Leu Arg Phe Asn Ser Ser Tyr Leu Gln Gly Thr Asn
    1490                1495                1500

Gln Ile Thr Gly Arg Tyr Glu Asp Gly Thr Leu Ser Leu Thr Ser Thr
1505                1510                1515                1520

Ser Asp Leu Gln Ser Gly Ile Ile Lys Asn Thr Ala Ser Leu Lys Tyr
                1525                1530                1535

Glu Asn Tyr Glu Leu Thr Leu Lys Ser Asp Thr Asn Gly Lys Tyr Lys
            1540                1545                1550

Asn Phe Ala Thr Ser Asn Lys Met Asp Met Thr Phe Ser Lys Gln Asn
        1555                1560                1565

Ala Leu Leu Arg Ser Glu Tyr Gln Ala Asp Tyr Glu Ser Leu Arg Phe
    1570                1575                1580

Phe Ser Leu Leu Ser Gly Ser Leu Asn Ser His Gly Leu Glu Leu Asn
1585                1590                1595                1600

Ala Asp Ile Leu Gly Thr Asp Lys Ile Asn Ser Gly Ala His Lys Ala
                1605                1610                1615

Thr Leu Arg Ile Gly Gln Asp Gly Ile Ser Thr Ser Ala Thr Thr Asn
            1620                1625                1630

Leu Lys Cys Ser Leu Leu Val Leu Glu Asn Glu Leu Asn Ala Glu Leu
        1635                1640                1645

Gly Leu Ser Gly Ala Ser Met Lys Leu Thr Thr Asn Gly Arg Phe Arg
    1650                1655                1660

Glu His Asn Ala Lys Phe Ser Leu Asp Gly Lys Ala Ala Leu Thr Glu
1665                1670                1675                1680
```

-continued

Leu Ser Leu Gly Ser Ala Tyr Gln Ala Met Ile Leu Gly Val Asp Ser
            1685                1690                1695

Lys Asn Ile Phe Asn Phe Lys Val Ser Gln Glu Gly Leu Lys Leu Ser
            1700                1705                1710

Asn Asp Met Met Gly Ser Tyr Ala Glu Met Lys Phe Asp His Thr Asn
            1715                1720                1725

Ser Leu Asn Ile Ala Gly Leu Ser Leu Asp Phe Ser Ser Lys Leu Asp
            1730                1735                1740

Asn Ile Tyr Ser Ser Asp Lys Phe Tyr Lys Gln Thr Val Asn Leu Gln
1745                1750                1755                1760

Leu Gln Pro Tyr Ser Leu Val Thr Thr Leu Asn Ser Asp Leu Lys Tyr
            1765                1770                1775

Asn Ala Leu Asp Leu Thr Asn Asn Gly Lys Leu Arg Leu Glu Pro Leu
            1780                1785                1790

Lys Leu His Val Ala Gly Asn Leu Lys Gly Ala Tyr Gln Asn Asn Glu
            1795                1800                1805

Ile Lys His Ile Tyr Ala Ile Ser Ser Ala Ala Leu Ser Ala Ser Tyr
            1810                1815                1820

Lys Ala Asp Thr Val Ala Lys Val Gln Gly Val Glu Phe Ser His Arg
1825                1830                1835                1840

Leu Asn Thr Asp Ile Ala Gly Leu Ala Ser Ala Ile Asp Met Ser Thr
            1845                1850                1855

Asn Tyr Asn Ser Asp Ser Leu His Phe Ser Asn Val Phe Arg Ser Val
            1860                1865                1870

Met Ala Pro Phe Thr Met Thr Ile Asp Ala His Thr Asn Gly Asn Gly
            1875                1880                1885

Lys Leu Ala Leu Trp Gly Glu His Thr Gly Gln Leu Tyr Ser Lys Phe
            1890                1895                1900

Leu Leu Lys Ala Glu Pro Leu Ala Phe Thr Phe Ser His Asp Tyr Lys
1905                1910                1915                1920

Gly Ser Thr Ser His His Leu Val Ser Arg Lys Ser Ile Ser Ala Ala
            1925                1930                1935

Leu Glu His Lys Val Ser Ala Leu Leu Thr Pro Ala Glu Gln Thr Gly
            1940                1945                1950

Thr Trp Lys Leu Lys Thr Gln Phe Asn Asn Asn Glu Tyr Ser Gln Asp
            1955                1960                1965

Leu Asp Ala Tyr Asn Thr Lys Asp Lys Ile Gly Val Glu Leu Thr Gly
            1970                1975                1980

Arg Thr Leu Ala Asp Leu Thr Leu Leu Asp Ser Pro Ile Lys Val Pro
1985                1990                1995                2000

Leu Leu Leu Ser Glu Pro Ile Asn Ile Ile Asp Ala Leu Glu Met Arg
            2005                2010                2015

Asp Ala Val Glu Lys Pro Gln Glu Phe Thr Ile Val Ala Phe Val Lys
            2020                2025                2030

Tyr Asp Lys Asn Gln Asp Val His Ser Ile Asn Leu Pro Phe Phe Glu
            2035                2040                2045

Thr Leu Gln Glu Tyr Phe Glu Arg Asn Arg Gln Thr Ile Ile Val Val
            2050                2055                2060

Leu Glu Asn Val Gln Arg Asn Leu Lys His Ile Asn Ile Asp Gln Phe
2065                2070                2075                2080

Val Arg Lys Tyr Arg Ala Ala Leu Gly Lys Leu Pro Gln Gln Ala Asn
            2085                2090                2095

-continued

```
Asp Tyr Leu Asn Ser Phe Asn Trp Glu Arg Gln Val Ser His Ala Lys
            2100                2105                2110
Glu Lys Leu Thr Ala Leu Thr Lys Lys Tyr Arg Ile Thr Glu Asn Asp
            2115                2120                2125
Ile Gln Ile Ala Leu Asp Asp Ala Lys Ile Asn Phe Asn Glu Lys Leu
            2130                2135                2140
Ser Gln Leu Gln Thr Tyr Met Ile Gln Phe Asp Gln Tyr Ile Lys Asp
2145                2150                2155                2160
Ser Tyr Asp Leu His Asp Leu Lys Ile Ala Ile Ala Asn Ile Ile Asp
            2165                2170                2175
Glu Ile Ile Glu Lys Leu Lys Ser Leu Asp Glu His Tyr His Ile Arg
            2180                2185                2190
Val Asn Leu Val Lys Thr Ile His Asp Leu His Leu Phe Ile Glu Asn
            2195                2200                2205
Ile Asp Phe Asn Lys Ser Gly Ser Ser Thr Ala Ser Trp Ile Gln Asn
            2210                2215                2220
Val Asp Thr Lys Tyr Gln Ile Arg Ile Gln Ile Gln Glu Lys Leu Gln
2225                2230                2235                2240
Gln Leu Lys Arg His Ile Gln Asn Ile Asp Ile Gln His Leu Ala Gly
            2245                2250                2255
Lys Leu Lys Gln His Ile Glu Ala Ile Asp Val Arg Val Leu Leu Asp
            2260                2265                2270
Gln Leu Gly Thr Thr Ile Ser Phe Glu Arg Ile Asn Asp Val Leu Glu
            2275                2280                2285
His Val Lys His Phe Val Ile Asn Leu Ile Gly Asp Phe Glu Val Ala
            2290                2295                2300
Glu Lys Ile Asn Ala Phe Arg Ala Lys Val His Glu Leu Ile Glu Arg
2305                2310                2315                2320
Tyr Glu Val Asp Gln Gln Ile Gln Val Leu Met Asp Lys Leu Val Glu
            2325                2330                2335
Leu Ala His Gln Tyr Lys Leu Lys Glu Thr Ile Gln Lys Leu Ser Asn
            2340                2345                2350
Val Leu Gln Gln Val Lys Ile Lys Asp Tyr Phe Glu Lys Leu Val Gly
            2355                2360                2365
Phe Ile Asp Asp Ala Val Lys Lys Leu Asn Glu Leu Ser Phe Lys Thr
            2370                2375                2380
Phe Ile Glu Asp Val Asn Lys Phe Leu Asp Met Leu Ile Lys Lys Leu
2385                2390                2395                2400
Lys Ser Phe Asp Tyr His Gln Phe Val Asp Glu Thr Asn Asp Lys Ile
            2405                2410                2415
Arg Glu Val Thr Gln Arg Leu Asn Gly Glu Ile Gln Ala Leu Glu Leu
            2420                2425                2430
Pro Gln Lys Ala Glu Ala Leu Lys Leu Phe Leu Glu Glu Thr Lys Ala
            2435                2440                2445
Thr Val Ala Val Tyr Leu Glu Ser Leu Gln Asp Thr Lys Ile Thr Leu
            2450                2455                2460
Ile Ile Asn Trp Leu Gln Glu Ala Leu Ser Ser Ala Ser Leu Ala His
2465                2470                2475                2480
Met Lys Ala Lys Phe Arg Glu Thr Leu Glu Asp Thr Arg Asp Arg Met
            2485                2490                2495
Tyr Gln Met Asp Ile Gln Gln Glu Leu Gln Arg Tyr Leu Ser Leu Val
            2500                2505                2510
Gly Gln Val Tyr Ser Thr Leu Val Thr Tyr Ile Ser Asp Trp Trp Thr
```

-continued

```
         2515                2520                2525
Leu Ala Ala Lys Asn Leu Thr Asp Phe Ala Glu Gln Tyr Ser Ile Gln
            2530                2535                2540
Asp Trp Ala Lys Arg Met Lys Ala Leu Val Glu Gln Gly Phe Thr Val
2545                2550                2555                2560
Pro Glu Ile Lys Thr Ile Leu Gly Thr Met Pro Ala Phe Glu Val Ser
                2565                2570                2575
Leu Gln Ala Leu Gln Lys Ala Thr Phe Gln Thr Pro Asp Phe Ile Val
            2580                2585                2590
Pro Leu Thr Asp Leu Arg Ile Pro Ser Val Gln Ile Asn Phe Lys Asp
            2595                2600                2605
Leu Lys Asn Ile Lys Ile Pro Ser Arg Phe Ser Thr Pro Glu Phe Thr
            2610                2615                2620
Ile Leu Asn Thr Phe His Ile Pro Ser Phe Thr Ile Asp Phe Val Glu
2625                2630                2635                2640
Met Lys Val Lys Ile Ile Arg Thr Ile Asp Gln Met Leu Asn Ser Glu
                2645                2650                2655
Leu Gln Trp Pro Val Pro Asp Ile Tyr Leu Arg Asp Leu Lys Val Glu
            2660                2665                2670
Asp Ile Pro Leu Ala Arg Ile Thr Leu Pro Asp Phe Arg Leu Pro Glu
            2675                2680                2685
Ile Ala Ile Pro Glu Phe Ile Ile Pro Thr Leu Asn Leu Asn Asp Phe
            2690                2695                2700
Gln Val Pro Asp Leu His Ile Pro Glu Phe Gln Leu Pro His Ile Ser
2705                2710                2715                2720
His Thr Ile Glu Val Pro Thr Phe Gly Lys Leu Tyr Ser Ile Leu Lys
                2725                2730                2735
Ile Gln Ser Pro Leu Phe Thr Leu Asp Ala Asn Ala Asp Ile Gly Asn
            2740                2745                2750
Gly Thr Thr Ser Ala Asn Glu Ala Gly Ile Ala Ala Ser Ile Thr Ala
            2755                2760                2765
Lys Gly Glu Ser Lys Leu Glu Val Leu Asn Phe Asp Phe Gln Ala Asn
            2770                2775                2780
Ala Gln Leu Ser Asn Pro Lys Ile Asn Pro Leu Ala Leu Lys Glu Ser
2785                2790                2795                2800
Val Lys Phe Ser Ser Lys Tyr Leu Arg Thr Glu His Gly Ser Glu Met
                2805                2810                2815
Leu Phe Phe Gly Asn Ala Ile Glu Gly Lys Ser Asn Thr Val Ala Ser
            2820                2825                2830
Leu His Thr Glu Lys Asn Thr Leu Glu Leu Ser Asn Gly Val Ile Val
            2835                2840                2845
Lys Ile Asn Asn Gln Leu Thr Leu Asp Ser Asn Thr Lys Tyr Phe His
            2850                2855                2860
Lys Leu Asn Ile Pro Lys Leu Asp Phe Ser Ser Gln Ala Asp Leu Arg
2865                2870                2875                2880
Asn Glu Ile Lys Thr Leu Leu Lys Ala Gly His Ile Ala Trp Thr Ser
                2885                2890                2895
Ser Gly Lys Gly Ser Trp Lys Trp Ala Cys Pro Arg Phe Ser Asp Glu
            2900                2905                2910
Gly Thr His Glu Ser Gln Ile Ser Phe Thr Ile Glu Gly Pro Leu Thr
            2915                2920                2925
Ser Phe Gly Leu Ser Asn Lys Ile Asn Ser Lys His Leu Arg Val Asn
            2930                2935                2940
```

-continued

```
Gln Asn Leu Val Tyr Glu Ser Gly Ser Leu Asn Phe Ser Lys Leu Glu
2945                2950                2955                2960

Ile Gln Ser Gln Val Asp Ser Gln His Val Gly His Ser Val Leu Thr
            2965                2970                2975

Ala Lys Gly Met Ala Leu Phe Gly Glu Gly Lys Ala Glu Phe Thr Gly
        2980                2985                2990

Arg His Asp Ala His Leu Asn Gly Lys Val Ile Gly Thr Leu Lys Asn
    2995                3000                3005

Ser Leu Phe Phe Ser Ala Gln Pro Phe Glu Ile Thr Ala Ser Thr Asn
3010                3015                3020

Asn Glu Gly Asn Leu Lys Val Arg Phe Pro Leu Arg Leu Thr Gly Lys
3025                3030                3035                3040

Ile Asp Phe Leu Asn Asn Tyr Ala Leu Phe Leu Ser Pro Ser Ala Gln
            3045                3050                3055

Gln Ala Ser Trp Gln Val Ser Ala Arg Phe Asn Gln Tyr Lys Tyr Ass
        3060                3065                3070

Gln Asn Phe Ser Ala Gly Asn Asn Glu Asn Ile Met Glu Ala His Val
    3075                3080                3085

Gly Ile Asn Gly Glu Ala Asn Leu Asp Phe Leu Asn Ile Pro Leu Thr
3090                3095                3100

Ile Pro Glu Met Arg Leu Pro Tyr Thr Ile Ile Thr Thr Pro Pro Leu
3105                3110                3115                3120

Lys Asp Phe Ser Leu Trp Glu Lys Thr Gly Leu Lys Glu Phe Leu Lys
            3125                3130                3135

Thr Thr Lys Gln Ser Phe Asp Leu Ser Val Lys Ala Gln Tyr Lys Lys
        3140                3145                3150

Asn Lys His Arg His Ser Ile Thr Asn Pro Leu Ala Val Leu Cys Glu
    3155                3160                3165

Phe Ile Ser Gln Ser Ile Lys Ser Phe Asp Arg His Phe Glu Lys Asn
    3170                3175                3180

Arg Asn Asn Ala Leu Asp Phe Val Thr Lys Ser Tyr Asn Glu Thr Lys
3185                3190                3195                3200

Ile Lys Phe Asp Lys Tyr Lys Ala Glu Lys Ser His Asp Glu Leu Pru
            3205                3210                3215

Arg Thr Phe Gln Ile Pro Gly Tyr Thr Val Pro Val Val Asn Val Glu
        3220                3225                3230

Val Ser Pro Phe Thr Ile Glu Met Ser Ala Phe Gly Tyr Val Phe Pro
    3235                3240                3245

Lys Ala Val Ser Met Pro Ser Phe Ser Ile Leu Gly Ser Asp Val Arg
3250                3255                3260

Val Pro Ser Tyr Thr Leu Ile Leu Pro Ser Leu Glu Leu Pro Val Leu
3265                3270                3275                3280

His Val Pro Arg Asn Leu Lys Leu Ser Leu Pro His Phe Lys Glu Leu
            3285                3290                3295

Cys Thr Ile Ser His Ile Phe Ile Pro Ala Met Gly Asn Ile Thr Tyr
        3300                3305                3310

Asp Phe Ser Phe Lys Ser Ser Val Ile Thr Leu Asn Thr Asn Ala Glu
    3315                3320                3325

Leu Phe Asn Gln Ser Asp Ile Val Ala His Leu Leu Ser Ser Ser Ser
3330                3335                3340

Ser Val Ile Asp Ala Leu Gln Tyr Lys Leu Glu Gly Thr Thr Arg Leu
3345                3350                3355                3360
```

-continued

```
Thr Arg Lys Arg Gly Leu Lys Leu Ala Thr Ala Leu Ser Leu Ser Asn
            3365                3370                3375

Lys Phe Val Glu Gly Ser His Asn Ser Thr Val Ser Leu Thr Thr Lys
        3380                3385                3390

Asn Met Glu Val Ser Val Ala Lys Thr Thr Lys Ala Glu Ile Pro Ile
        3395                3400                3405

Leu Arg Met Asn Phe Lys Gln Glu Leu Asn Gly Asn Thr Lys Ser Lys
        3410                3415                3420

Pro Thr Val Ser Ser Met Glu Phe Lys Tyr Asp Phe Asn Ser Ser
3425                3430                3435                3440

Met Leu Tyr Ser Thr Ala Lys Gly Ala Val Asp His Lys Leu Ser Leu
            3445                3450                3455

Glu Ser Leu Thr Ser Tyr Phe Ser Ile Glu Ser Ser Thr Lys Gly Asp
            3460                3465                3470

Val Lys Gly Ser Val Leu Ser Arg Glu Tyr Ser Gly Thr Ile Ala Ser
            3475                3480                3485

Glu Ala Asn Thr Tyr Leu Asn Ser Lys Ser Thr Arg Ser Ser Val Lys
            3490                3495                3500

Leu Gln Gly Thr Ser Lys Ile Asp Asp Ile Trp Asn Leu Glu Val Lys
3505                3510                3515                3520

Glu Asn Phe Ala Gly Glu Ala Thr Leu Gln Arg Ile Tyr Ser Leu Trp
            3525                3530                3535

Glu His Ser Thr Lys Asn His Leu Gln Leu Glu Gly Leu Phe Phe Thr
            3540                3545                3550

Asn Gly Glu His Thr Ser Lys Ala Thr Leu Glu Leu Ser Pro Trp Gln
            3555                3560                3565

Met Ser Ala Leu Val Gln Val His Ala Ser Gln Pro Ser Ser Phe His
            3570                3575                3580

Asp Phe Pro Asp Leu Gly Gln Glu Val Ala Leu Asn Ala Asn Thr Lys
3585                3590                3595                3600

Asn Gln Lys Ile Arg Trp Lys Asn Glu Val Arg Ile His Ser Gly Ser
            3605                3610                3615

Phe Gln Ser Gln Val Glu Leu Ser Asn Asp Gln Glu Lys Ala His Leu
            3620                3625                3630

Asp Ile Ala Gly Ser Leu Glu Gly His Leu Arg Phe Leu Lys Asn Ile
            3635                3640                3645

Ile Leu Pro Val Tyr Asp Lys Ser Leu Trp Asp Phe Leu Lys Leu Asp
            3650                3655                3660

Val Thr Thr Ser Ile Gly Arg Arg Gln His Leu Arg Val Ser Thr Ala
3665                3670                3675                3680

Phe Val Tyr Thr Lys Asn Pro Asn Gly Tyr Ser Phe Ser Ile Pro Val
            3685                3690                3695

Lys Val Leu Ala Asp Lys Phe Ile Thr Pro Gly Leu Lys Leu Asn Asp
            3700                3705                3710

Leu Asn Ser Val Leu Val Met Pro Thr Phe His Val Pro Phe Thr Asp
            3715                3720                3725

Leu Gln Val Pro Ser Cys Lys Leu Asp Phe Arg Glu Ile Gln Ile Tyr
            3730                3735                3740

Lys Lys Leu Arg Thr Ser Ser Phe Ala Leu Asn Leu Pro Thr Leu Pro
3745                3750                3755                3760

Glu Val Lys Phe Pro Glu Val Asp Val Leu Thr Lys Tyr Ser Gln Pro
            3765                3770                3775

Glu Asp Ser Leu Ile Pro Phe Phe Glu Ile Thr Val Pro Glu Ser Gln
```

```
                   3780              3785              3790
Leu Thr Val Ser Gln Phe Thr Leu Pro Lys Ser Val Ser Asp Gly Ile
        3795              3800              3805
Ala Ala Leu Asp Leu Asn Ala Val Ala Asn Lys Ile Ala Asp Phe Glu
    3810              3815              3820
Leu Pro Thr Ile Ile Val Pro Glu Gln Thr Ile Glu Ile Pro Ser Ile
3825              3830              3835              3840
Lys Phe Ser Val Pro Ala Gly Ile Val Ile Pro Ser Phe Gln Ala Leu
            3845              3850              3855
Thr Ala Arg Phe Glu Val Asp Ser Pro Val Tyr Asn Ala Thr Trp Ser
            3860              3865              3870
Ala Ser Leu Lys Asn Lys Ala Asp Tyr Val Glu Thr Val Leu Asp Ser
        3875              3880              3885
Thr Cys Ser Ser Thr Val Gln Phe Leu Glu Tyr Glu Leu Asn Val Leu
        3890              3895              3900
Gly Thr His Lys Ile Glu Asp Gly Thr Leu Ala Ser Lys Thr Lys Gly
3905              3910              3915              3920
Thr Leu Ala His Arg Asp Phe Ser Ala Glu Tyr Glu Glu Asp Gly Lys
            3925              3930              3935
Phe Glu Gly Leu Gln Glu Trp Glu Gly Lys Ala His Leu Asn Ile Lys
            3940              3945              3950
Ser Pro Ala Phe Thr Asp Leu His Leu Arg Tyr Gln Lys Asp Lys Lys
            3955              3960              3965
Gly Ile Ser Thr Ser Ala Ala Ser Pro Ala Val Gly Thr Val Gly Met
        3970              3975              3980
Asp Met Asp Glu Asp Asp Phe Ser Lys Trp Asn Phe Tyr Tyr Ser
3985              3990              3995              4000
Pro Gln Ser Ser Pro Asp Lys Lys Leu Thr Ile Phe Lys Thr Glu Leu
            4005              4010              4015
Arg Val Arg Glu Ser Asp Glu Glu Thr Gln Ile Lys Val Asn Trp Glu
            4020              4025              4030
Glu Glu Ala Ala Ser Gly Leu Leu Thr Ser Leu Lys Asp Asn Val Pro
        4035              4040              4045
Lys Ala Thr Gly Val Leu Tyr Asp Tyr Val Asn Lys Tyr His Trp Glu
    4050              4055              4060
His Thr Gly Leu Thr Leu Arg Glu Val Ser Ser Lys Leu Arg Arg Asn
4065              4070              4075              4080
Leu Gln Asn Asn Ala Glu Trp Val Tyr Gln Gly Ala Ile Arg Gln Ile
            4085              4090              4095
Asp Asp Ile Asp Val Arg Phe Gln Lys Ala Ala Ser Gly Thr Thr Gly
        4100              4105              4110
Thr Tyr Gln Glu Trp Lys Asp Lys Ala Gln Asn Leu Tyr Gln Glu Leu
            4115              4120              4125
Leu Thr Gln Glu Gly Gln Ala Ser Phe Gln Gly Leu Lys Asp Asn Val
        4130              4135              4140
Phe Asp Gly Leu Val Arg Val Thr Gln Lys Phe His Met Lys Val Lys
4145              4150              4155              4160
His Leu Ile Asp Ser Leu Ile Asp Phe Leu Asn Phe Pro Arg Phe Gln
            4165              4170              4175
Phe Pro Gly Lys Pro Gly Ile Tyr Thr Arg Glu Glu Leu Cys Thr Met
            4180              4185              4190
Phe Ile Arg Glu Val Gly Thr Val Leu Ser Gln Val Tyr Ser Lys Val
        4195              4200              4205
```

-continued

```
His Asn Gly Ser Glu Ile Leu Phe Ser Tyr Phe Gln Asp Leu Val Ile
        4210                4215                4220
Thr Leu Pro Phe Glu Leu Arg Lys His Lys Leu Ile Asp Val Ile Ser
4225            4230                4235                    4240
Met Tyr Arg Glu Leu Leu Lys Asp Leu Ser Lys Glu Ala Gln Glu Val
            4245                4250                4255
Phe Lys Ala Ile Gln Ser Leu Lys Thr Thr Glu Val Leu Arg Asn Leu
            4260                4265                4270
Gln Asp Leu Leu Gln Phe Ile Phe Gln Leu Ile Glu Asp Asn Ile Lys
        4275                4280                4285
Gln Leu Lys Glu Met Lys Phe Thr Tyr Leu Ile Asn Tyr Ile Gln Asp
        4290                4295                4300
Glu Ile Asn Thr Ile Phe Asn Asp Tyr Ile Pro Tyr Val Phe Lys Leu
4305            4310                4315                    4320
Leu Lys Glu Asn Leu Cys Leu Asn Leu His Lys Phe Asn Glu Phe Ile
            4325                4330                4335
Gln Asn Glu Leu Gln Glu Ala Ser Gln Glu Leu Gln Gln Ile His Gln
            4340                4345                4350
Tyr Ile Met Ala Leu Arg Glu Glu Tyr Phe Asp Pro Ser Ile Val Gly
        4355                4360                4365
Trp Thr Val Lys Tyr Tyr Glu Leu Glu Glu Lys Ile Val Ser Leu Ile
        4370                4375                4380
Lys Asn Leu Leu Val Ala Leu Lys Asp Phe His Ser Glu Tyr Ile Val
4385            4390                4395                    4400
Ser Ala Ser Asn Phe Thr Ser Gln Leu Ser Ser Gln Val Glu Gln Phe
                4405                4410                4415
Leu His Arg Asn Ile Gln Glu Tyr Leu Ser Ile Leu Thr Asp Pro Asp
            4420                4425                4430
Gly Lys Gly Lys Glu Lys Ile Ala Glu Leu Ser Ala Thr Ala Gln Glu
            4435                4440                4445
Ile Ile Lys Ser Gln Ala Ile Ala Thr Lys Lys Ile Ile Ser Asp Tyr
        4450                4455                4460
His Gln Gln Phe Arg Tyr Lys Leu Gln Asp Phe Ser Asp Gln Leu Ser
4465            4470                4475                    4480
Asp Tyr Tyr Glu Lys Phe Ile Ala Glu Ser Lys Arg Leu Ile Asp Leu
                4485                4490                4495
Ser Ile Gln Asn Tyr His Thr Phe Leu Ile Tyr Ile Thr Glu Leu Leu
            4500                4505                4510
Lys Lys Leu Gln Ser Thr Thr Val Met Asn Pro Tyr Met Lys Leu Ala
        4515                4520                4525
Pro Gly Glu Leu Thr Ile Ile Leu
    4530            4535
```